(12) United States Patent
Mylonakis et al.

(10) Patent No.: US 9,320,751 B2
(45) Date of Patent: Apr. 26, 2016

(54) MODIFIED SAPONINS FOR THE TREATMENT OF FUNGAL INFECTIONS

(71) Applicants: The General Hospital Corporation, Boston, MA (US); The Broad Institute, Inc., Cambridge, MA (US); Massachusetts Institute of Technology, Cambridge, MA (US)

(72) Inventors: Eleftherios Mylonakis, Boston, MA (US); Edward Holson, Newton Highlands, MA (US); Frederick M. Ausubel, Newton, MA (US)

(73) Assignees: The General Hospital Corporation, Boston, MA (US); The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/620,542

(22) Filed: Feb. 12, 2015

(65) Prior Publication Data
US 2015/0182544 A1 Jul. 2, 2015

Related U.S. Application Data

(62) Division of application No. 13/521,267, filed as application No. PCT/US2011/020779 on Jan. 11, 2011, now Pat. No. 8,987,217.

(60) Provisional application No. 61/294,304, filed on Jan. 12, 2010.

(51) Int. Cl.
*A61K 31/704* (2006.01)
*A61K 31/7048* (2006.01)

(52) U.S. Cl.
CPC ........... *A61K 31/704* (2013.01); *A61K 31/7048* (2013.01)

(58) Field of Classification Search
None
See application file for complete search history.

(56) References Cited

U.S. PATENT DOCUMENTS 6,310,091 B1 10/2001 De Lucca, II et al.

FOREIGN PATENT DOCUMENTS

WO 2005/117925 12/2005

OTHER PUBLICATIONS

Zhang et al., Journal of Ethnopharmacology, 103, 2006, pp. 76-84.*
Takechi et al., Phytochemistry, vol. 41(1), pp. 121-123, 1996.*
Bangham et al., "Action of saponin on biological cell membranes," Nature, 196:952-953(1962).
Berman and Sudbery, "Candida albicans: A molecular revolution built on lessons from budding yeast," Nat Rev Genet., 3:918-932 (2002).
Blankenship and Mitchell, "How to build a biofilm: a fungal perspective," Curr Opin Microbiol., 9:588-594 (2006).
Breger et al., "Antifungal chemical compounds identified using a C. elegans pathogenicity assay," PLoS Pathog, 3:e18, pp. 0168-0178 (2007).
Carotenuto et al., "Spirostanol saponins of Allium porrum L," Phytochem., 51:1077-1082 (1999).
Corsello et al., "An epidemiological survey of vulvovaginal candidiasis in Italy," Eur J Obstet Gynecol Reprod Biol., 110:66-72 (2003).
d'Enfert, "Biofilms and their role in the resistance of pathogenic Candida to antifungal agents," Curr Drug Targets, 7:465-470 (2006).
Davis et al., "Candida albicans RIM101 pH response pathway is required for host-pathogen interactions," Infect Immun., 68:5953-5959 (2000).
Demidova and Hamblin, "Photodynamic therapy targeted to pathogens," Int J Immunopathol Pharmacol., 17:245-254 (2004).
Dixon, "Natural products and plant disease resistance," Nature, 411:843-847 (2001).
Edmond et al., "Nosocomial bloodstream infections in United States hospitals: a three year analysis," Clin. Infect Dis., 29:239-244 (1999).
Enomot et al., "Positive inotropic action of saponins on isolated atrial and papillary muscles from the guinea pig," Br J Pharmac., 88(1):259-67 (19860.
Francis et al., "The biological action of saponins in animal systems: a review," Br J Nutrition, 88:587-605 (2002).
Fuchs et al., "Susceptibility of Cryptococcus neoformans to photodynamic inactivation is associated with cell wall integrity," Antimicrob Agents Chemother, 51:2929-2936 (2007).
Galgiani et al., "Reference method for broth dilution susceptibility testing of yeasts.; Approved Standard M27-A," National Committee for Clinical Laboratory Standards, 45 pages (Jun. 1997).
Garcia-Effron et al., "Correlating echinocandin MIC and kinetic inhibition of fks1 mutant glucan synthases for Candida albicans: implications for interpretive breakpoints," Antimicrob Agents Chemother, 53:112-122 (2009).
Germonprez et al., "In vitro and in vivo anti-leishmanial activity of triterpenoid saponins isolated from Maesa balansae and some chemical derivatives," J Med Chem., 48:32-37 (2005).
Glauert et al., "Action of saponin on biological cell membranes," Nature, 953-955 (1962).
Gold et al., "Amphotericin A and B, antifungal antibiotics produced by a streptomycete. I. In vitro studies of A," Antibiotics Ann, 579-586 (1955-1956).
Hamblin and Hasan, "Photodynamic therapy: a new antimicrobial approach to infectious disease?" Photochem Photobiol Sci., 3:436-450 (Author Manuscript) (2004).
Herlt et al., "Two major saponins from seeds of Barringtonia asiatica: putative antifeedants toward *Epilachna* sp larvae," J Nat Prod., 65:115-120 (2002).
Honda et al., "Periodate oxidation analysis of carbohydrates. Part XII. Studies of the structures of the carbohydrate components in plant oligosaccharide glycosides by the dithioacetal method," Carbohydrate Res., 73:135-43 (1979).

(Continued)

*Primary Examiner* — Traviss C McIntosh, III
(74) *Attorney, Agent, or Firm* — Fish & Richardson P.C.

(57) ABSTRACT

Methods of treating a fungal infection in a subject, the method comprising administering to the subject a modified saponin.

6 Claims, 8 Drawing Sheets

(56) References Cited

OTHER PUBLICATIONS

Honda et al., "Periodate oxidation analysis of carbohydrates. Part 12. Rapid determination of aldehydes in the oxidation products of oligoglycosides by the dithioacetal method," Analytica Chimica Acta, 105(1):153-61 (1979).
International Search Report and Written Opinion issued Oct. 12, 2011 in international application No. PCT/US2011/020779, 5 pgs.
Itoh et al., "Metallothionein induction and hepatoprotection by echinoside A and Sakuraso-saponin," Phytotherapy Res., 11(2):132-135 (1997).
Itoh et al., "Metallothionein-independent hepatoprotection by zinc and sakuraso-saponin," Toxicology Lett., 93(2,3):135-140 (1997).
Jett et al., "Simplified Agar Plate Method for Quantifying Viable Bacteria," Biotechniques, 23:648-650 (1997).
Kitagawa et al., "A new selective cleavage method of glucuronide linkage in oligoglycosides. Lead tetraacetate oxidation followed by alkali treatment," Tetra Lett., 7:549-52 (1976).
Kitagawa et al., "Chemical transformation of uronic acids leading to aminocyclitols. V. Synthesis of aminocyclitol-oligosides from glucuronide-saponins by means of lead tetraacetate oxidation," Chem Pharma Bull., 32(12):4858-65 (1984).
Kitagawa et al., "Chemical transformation of uronic acids leading to aminocyclitols. III. Syntheses of aminocyclitols and aminocyclitol-oligoglycosides from uronic acids and glucuronide-saponins by means of electrolytic decarboxylation," Chem Pharma Bull., 29(9):2571-81 (1981).
Kitagawa et al., "Saponin and sapogenol. XVII. Structure of Sakuraso-saponin, a pentaglycoside of protoprimulagenin A from the root of Primula sieboldi E. Morren," Chem Pharma Bull., 24(10):2470-9 (1976).
Kitagawa et al., "Saponin and sapogenol. XX. Selective cleavage of the glucuronide linkage in saponin by acetic anhydride and pyridine treatment," Chem Pharma Bull., 25(6):1408-16 (1977).
Kitagawa et al., "Saponin and sapogenol. XXIX. Selective cleavage of the glucuronide linkage in oligoglycosides by anodic oxidation," Chem Pharma Bull., 28(10):3078-86 (1980).
Kitagawa et al., "Saponin and sapogenol. XXVIII. Reinvestigation of the branching positions in the glucuronide moieties of three glucuronide saponins: desacyl-jegosaponin, desacyl-boninsaponin A, and sakuraso-saponin," Chem Pharma Bull., 28(1):296-300 (1980).
Kitagawa et al., "Syntheses of aminocyclitols and aminocyclitol-oligoglycosides from uronic acids and glucuronide-saponins by means of an electrolytic decarboxylation reaction," Heterocycles, 15(1):349-54 (1981).
Kobayashi and Cutler, "Candida albicans hyphal formation and virulence: is there a clearly defined role?" Trends Microbiol., 6:92-94 (1998).
Kojic and Darouiche, "Candida infections of medical devices," Clin Microbiol Rev., 17:255-267 (2004).
Kumamoto and Vinces, "Alternative Candida albicans lifestyles: Growth on surfaces," Annu Rev Microbiol., 59:113-133 (2005).
Kumamoto, "Candida biofilms," Curr Opin Microbiol., 5:608-611 (2002).
Laupland et al., "Incidence and risk factors for acquiring nosocomial urinary tract infection in the critically ill," J Crit Care, 17:50-57 (2002).
Lavaud, et al., "Sakurasosaponin from Tapeinosperma clethroides," de Pharmacie, Reims, 70(1):116-118 (1999).
Li et al., "Quantitative variation of biofilms among strains in natural populations of Candida albicans," Micriobiol., 149:353-362 (2003).
Liu et al., "A new triterpenoid spaonin isolated from the seeds of Aesculus assamica Griff," Chinese Chem Lett., 17:211-214 (2006).
Moy et al., "Identification of novel antimicrobials using a live-animal infection model," PNAS, 103:10414-10419 (2006).

Ohtani et al., "Molluscicidal and antifungal triterpenoid saponins from Rapanea melanophloeos leaves," Phytochem., 33:83-86 (1993).
Okoli et al., "Identification of antifungal compounds active against Candida albicans using an improved high-throughput Caenorhabditis elegans assay," PLoS ONE, 4:e7025 (2009).
Osbourn, "Saponins and plant defence—a soap story," Trends Plant Sci., 1:4-9 (1996).
Paulitsch et al., "A 5-year (2000-2004) epidemiological survey of Candida and non-Candida yeast species causing vulvovaginal candidiasis in Graz, Austria," Mycoses, 49:471-475 (2006).
Pfaller et al., "Epidemiology of invasive candidiasis: a persistent public health problem," Clin Microbiol. Rev., 20:133-163 (2007).
Raad, "The Pathogenesis and prevention of central venous catheter-related infections," Middle East J Anesthesiol., 12:381-403 (1994).
Ramage et al., "Candida biofilms on implanted biomaterials: a clinically significant problem," FEMS Yeast Res., 6:979-986 (2006).
Richard et al., "Candida albicans biofilm-defective mutants," Eukaryot Cell, 4:1493-1502 (2005).
Sata et al., "New antifungal and cytotoxic steroidal saponins from the bulbs of an elephant garlic mutant," Biosci Biotechnol Biochem., 62:1904-1911 (1998).
Simons et al., "Dual effects of plant steroidal alkaloids on *Saccharomyces cerevisiae*," Antimicrob Agents Chemother, 50:2732-2740 (2006).
Spanakis et al., "New agents for the treatment of fungal infections: clinical efficacy and gaps in coverage," Clin Infect Dis, 43:1060-1068 (2006).
Sparg et al., "Biological activities and distribution of plant saponins," J Ethnopharmacol., 94:219-243 (2004).
Sun et al., "Advances in saponin-based adjuvants," Vaccine, 27:1787-1796 (2009).
Takechi et al., "Time course differences between steroid and triterpenoid saponins," Planta Med., 61:76-77 (1995).
Tampakakis et al., "A C. elegans-based, whole animal, in vivo screen for the identification of antifungal compounds," Nat Protocol., 3:1925-1931 (2008).
Tegos and Hamlin., "Phenothiazinium antimicrobial photosensitizers are substrates of bacterial multidrug resistance pumps," Antimicrob Agents Chemother, 50:196-203 (2006).
Tegos et al., "Protease-stable polycationic photosensitizer conjugates between polyethyleneimine and chlorin(e6) for broad-spectrum antimicrobial photoinactivation," Antimicrob Agents Chemother, 50:1402-1410 (2006).
Trejo and Bennett, "*Streptomyces nodosus* sp. N, the amphotericin-producing organism," J Bacteriol., 85:436-439 (1963).
Ventolini et al., "Vulvovaginal candidiasis from non-albicans species: retrospective study of recurrence rate after fluconazole therapy," J Repord Med., 51:475-478 (2006).
Voutquenne et al., "Structure-activity relationships of haemolytic saponins," Pharma Biol., 40(4):253-262 (2002).
White et al., "Resistance mechanisms in clinical isolates of Candida albicans," Antimicrob Agents Chemother, 46:1704-1713 (2002).
Yamasaki et al., "Alterations by saponins of passive calcium permeability and sodium-calcium exchange activity of canine cardiac sarcolemmal vesicles," Biochimica et Biophysica Acta, Biomembranes, 897(3):481-7 (1987).
Yang et al., "Antifungal Activity of C-27 Steroidal Saponins," Antimicrobial Agents and Chemotherapy, 50(5):1710-1714 (May 2006).
Zhang et al., "Antifungal activities and action mechanisms of compounds from Tribulus terrestris L.," Journal of Ethnopharmacology, 103:76-84 (2005).
Zhang et al., "In vitro and in vivo antifungal activities of the eight steroid saponins from Tribulus terrestris L. with potent activity against fluconazole-resistant fungal," Biol Pharm Bull., 28:2211-2215 (2005).

* cited by examiner

R₂ = OH, R₃ = H;  % surv = 80%

R₂, R₃ = OAc;  % surv = 93%

A19  R₁ =

A25  R₁ =

BARRIGENOL FAMILY

MODIFIED SAPONINS FOR THE TREATMENT OF FUNGAL INFECTIONS

CLAIM OF PRIORITY

This application is a divisional of U.S. patent application Ser. No. 13/521,267, filed on Jul. 10, 2012, which is a U.S. National Phase Application under 35 U.S.C. 371 of International Application No. PCT/US2011/020779, filed on Jan. 11, 2011, which claims the benefit of U.S. Provisional Patent Application Ser. No. 61/294,304, filed on Jan. 12, 2010, the contents of each of which are hereby incorporated by reference in their entireties.

FEDERALLY SPONSORED RESEARCH OR DEVELOPMENT

This invention was made with Government support under Grant No. R01 AI075286 awarded by the National Institutes of Health, and the National Cancer Institute's Initiative for Chemical Genetics under contract #N01-CO-12400. The Government has certain rights in the invention.

TECHNICAL FIELD

This invention relates to methods of treating fungal infections using saponins disclosed herein.

BACKGROUND

Fungal infections are a major cause of morbidity and mortality and there is an urgent need for the development of new antifungal agents. Candidiasis is the most common fungal infection and *Candida* spp. have become the fourth leading cause of bloodstream infections in the United States (Edmond et al., Clin Infect Dis, 29:239-244 (1999); Pfaller et al., Clin Microbiol Rev, 20:133-163 (2007)). In addition to the morbidity and mortality associated with systemic candidiasis, localized infections are also a significant health issue. *Candida* spp. are the second most common cause of urinary tract infection (Laupland et al., J Crit Care, 17:50-57 (2002)) and according to different studies, approximately 70% of women experience vaginal infections caused by *Candida* spp., 20% of them suffer from recurrent infections, and of these latter recurrent infections, about half of the patients have four or more episodes per year (Paulitsch et al., Mycoses, 49:471-475 (2006); Corsello et al., Eur J Obstet Gynecol Reprod Biol, 110:66-72 (2003); Ventolini et al., J Reprod Med, 51:475-478 (2006)).

The success of *Candida albicans* as a human pathogen is a result of their diverse armamentarium of virulence factors. *C. albicans* colonizes mucosal surfaces, such as the gastrointestinal tract (isolated from over half of the oral cavities of healthy adults) and vaginal epithelium (Paulitsch et al., Mycoses, 49:471-475 (2006); Kumamoto et al., Annu Rev Microbiol, 59:113-133 (2005); Li et al., Microbiology, 149:353-362 (2003)). *Candida* virulence is a result of its ability to form biofilms, switch between different forms, and produce filaments in response to environmental conditions (Berman et al., Nat Rev Genet, 3:918-932 (2002); Kobayashi et al., Trends Microbiol, 6:92-94 (1998)). *Candida* biofilm formation has important clinical repercussions because of their increased resistance to antifungal therapy and the ability of cells within biofilms to withstand host immune defenses, resulting in treatment failure and the need to remove catheters and other biological materials (Kumamoto et al., Annu Rev Microbiol, 59:113-133 (2005); Kojic et al., Clin Microbiol Rev, 17:255-267 (2004); Raad, Middle East J Anesthesiol, 12:381-403 (1994); Ramage et al., FEMS Yeast Res, 6:979-986 (2006); Richard et al., Eukaryot Cell, 4:1493-1502 (2005)).

SUMMARY

The present invention is based, at least in part, on the discovery of saponins that are active antifungals; without wishing to be bound by theory, it is believed that these saponins exert their activity either directly and/or by enhancing the host antifungal responses. Thus, described herein are compounds for use in the treatment of fungal infections, e.g., *Candida* infections. Also described are methods for treating fungal infections, e.g., *Candida* infections, by administering a therapeutically effective amount of a saponin as described herein.

In one aspect, provided herein are compounds selected from the group consisting of aginosides, arvensoside B, barrigenols, sakurasosaponins and maesabalides for use in the treatment of fungal infections. Also provided are methods of treating a fungal infection in a subject. The methods include administering to the subject a therapeutically effective amount of a saponin, e.g., a compound selected from the group consisting of aginosides, arvensoside B, barrigenols, sakurasosaponins and maesabalides.

In another aspect, the present invention features methods for treating fungal infections in a subject, by administering a compound of Formula I:

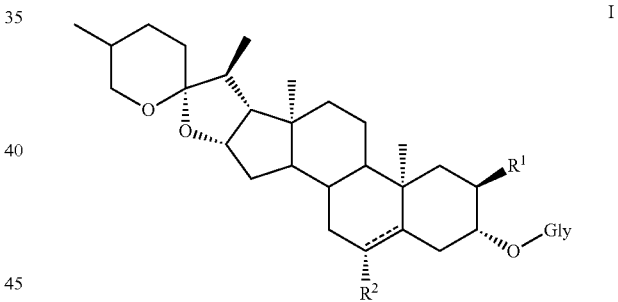

or a pharmaceutically acceptable salt thereof, wherein:
$R^1$ and $R^2$ are each independently H or OH;
Gly is

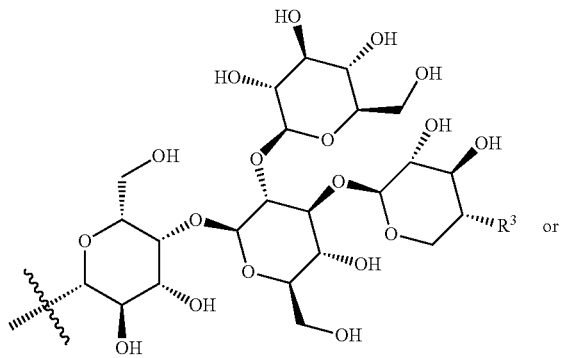

or

-continued
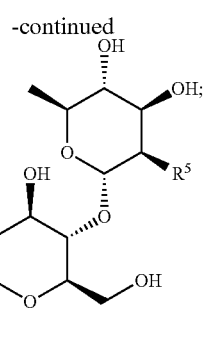
$R^3$ is OH or
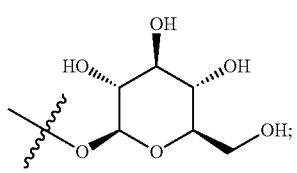 [SMILES: *O[C@@H]1O[C@H](CO)[C@@H](O)[C@H](O)[C@H]1O]
$R^4$ and $R^5$ are each independently OH or
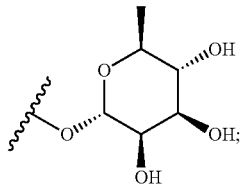 [SMILES: *O[C@@H]1O[C@@H](C)[C@H](O)[C@@H](O)[C@H]1O]
and
⌇ denotes either a single bond or a double-bond.
In some embodiments, the compound is:
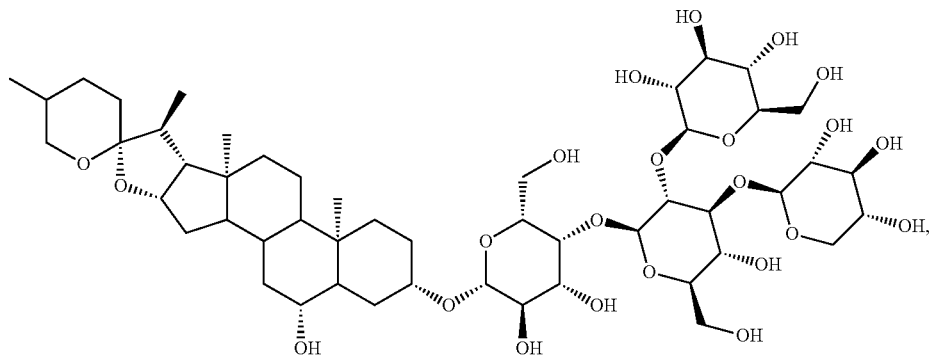 [SMILES: CC1CC[C@@]2(OC1)O[C@H]1CC3C4C[C@@H](O)C5C[C@@H](O[C@@H]6O[C@H](CO)[C@H](O[C@@H]7O[C@H](CO)[C@@H](O)[C@H](O[C@@H]8OC[C@@H](O)[C@H](O)[C@H]8O)[C@H]7O[C@@H]7O[C@H](CO)[C@@H](O)[C@H](O)[C@H]7O)[C@H](O)[C@H]6O)CC[C@]5(C)C4CC[C@]3(C)[C@H]1[C@@H]2C]
or a pharmaceutically acceptable salt thereof.
In some embodiments, the compound is:
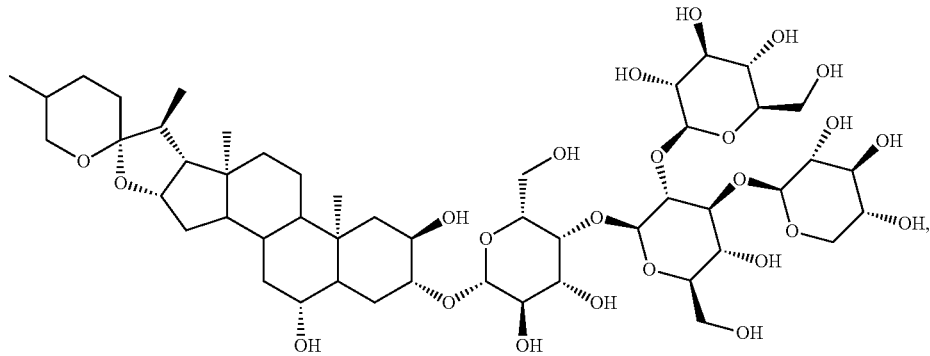 [SMILES: CC1CC[C@@]2(OC1)O[C@H]1CC3C4C[C@@H](O)C5C[C@@H](O[C@@H]6O[C@H](CO)[C@H](O[C@@H]7O[C@H](CO)[C@@H](O)[C@H](O[C@@H]8OC[C@@H](O)[C@H](O)[C@H]8O)[C@H]7O[C@@H]7O[C@H](CO)[C@@H](O)[C@H](O)[C@H]7O)[C@H](O)[C@H]6O)[C@H](O)C[C@]5(C)C4CC[C@]3(C)[C@H]1[C@@H]2C]
or a pharmaceutically acceptable salt thereof.

In some embodiments, the compound is:

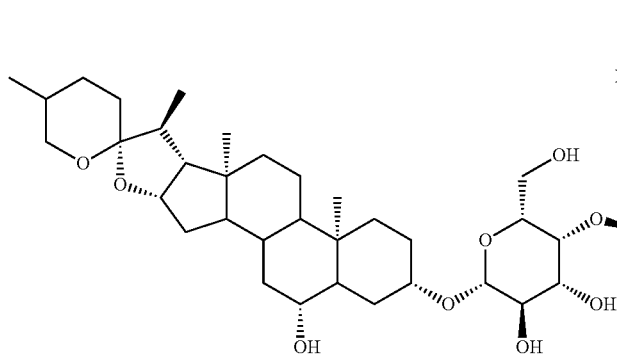

or a pharmaceutically acceptable salt thereof.

In some embodiments, the compound is:

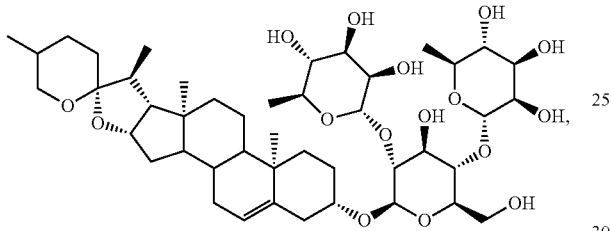

or a pharmaceutically acceptable salt thereof.

In some embodiments, the compound is:

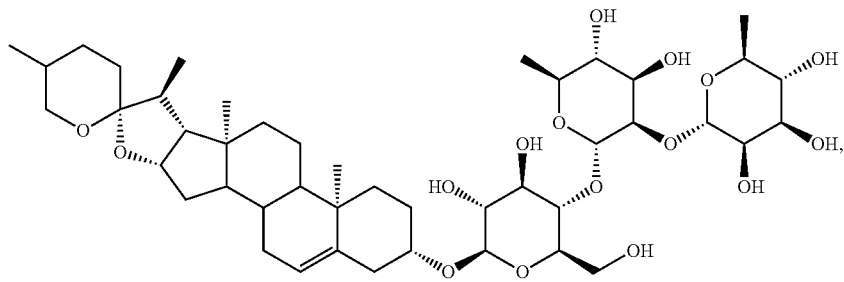 [SMILES: CC1CC[C@@]2(OC1)O[C@H]1CC3C4CC=C5C[C@@H](O[C@@H]6O[C@H](CO)[C@@H](O[C@@H]7O[C@@H](C)[C@H](O)[C@@H](O)[C@H]7O[C@@H]7O[C@@H](C)[C@H](O)[C@@H](O)[C@H]7O)[C@H](O)[C@H]6O)CC[C@]5(C)C4CC[C@]3(C)[C@H]1[C@@H]2C]

or a pharmaceutically acceptable salt thereof.

In another aspect, the invention provides methods for treating a fungal infection in a subject. The methods include administering a compound of Formula II:

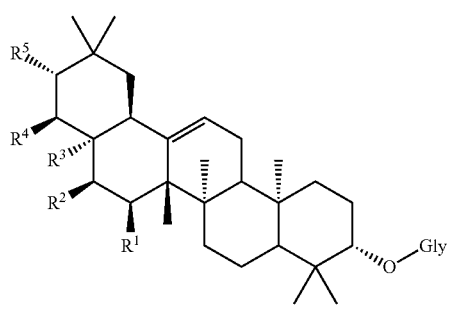

or a pharmaceutically acceptable salt thereof, wherein:

$R_1$ is H or $OC(O)R^A$;

$R_2$ is H or OH;

$R_3$ is H, $C(O)OR^A$, $CH_2OR^A$, $CH_2OC(O)R^A$;

$R_4$ and $R_5$ are each independently H or $OC(O)R^B$;

$R^A$ is H or $C_{1-6}$ alkyl;

$R^B$ is $C_{2-6}$ alkenyl; and

Gly is

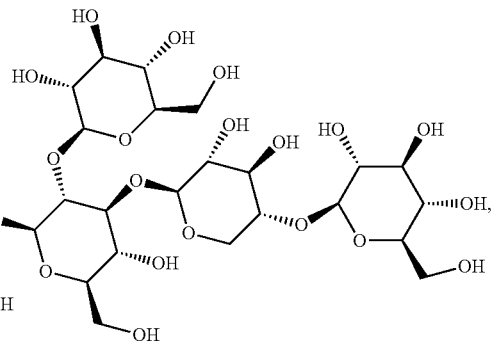

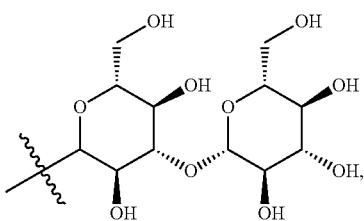

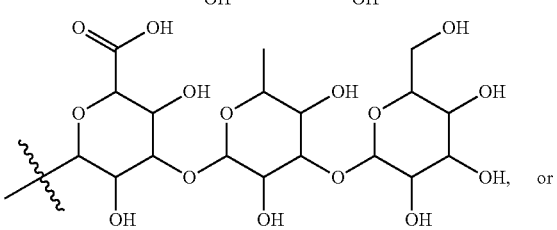, or

-continued
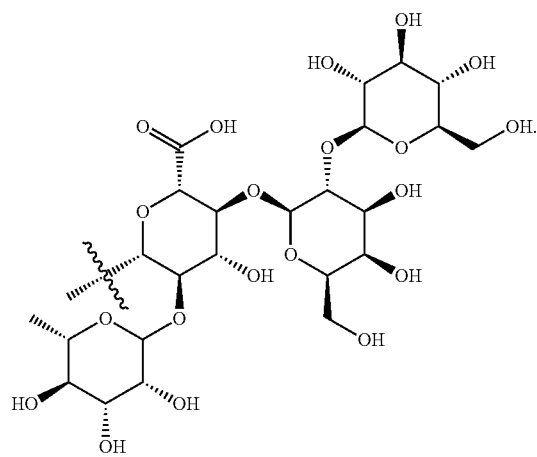
In some embodiments, the compound is:
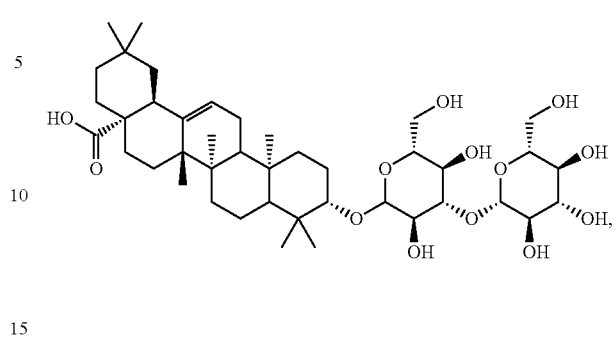
or a pharmaceutically acceptable salt thereof.
In some embodiments, the compound is:
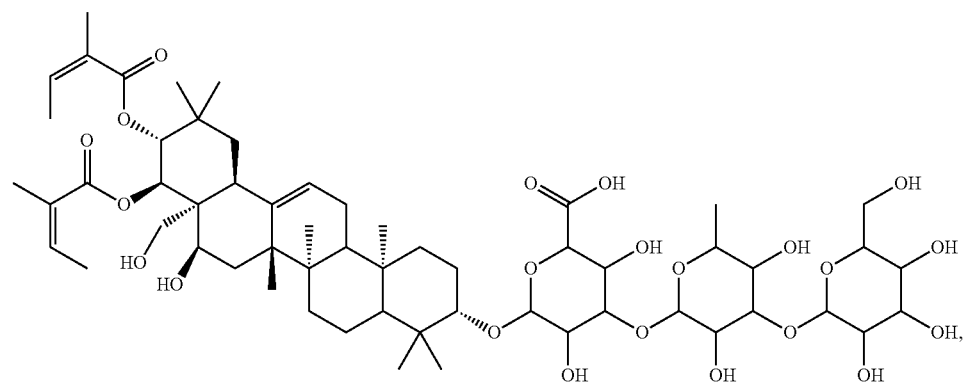
or a pharmaceutically acceptable salt thereof.
In some embodiments, the compound is:
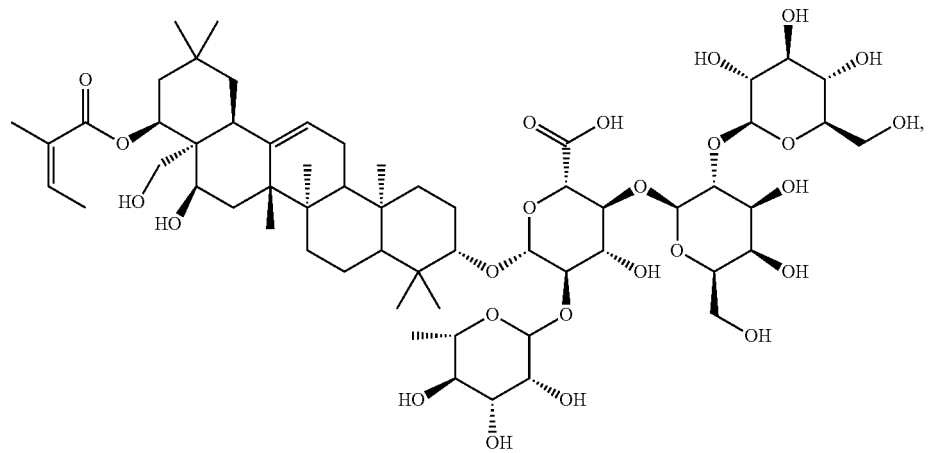
or a pharmaceutically acceptable salt thereof.

In some embodiments, the compound is:

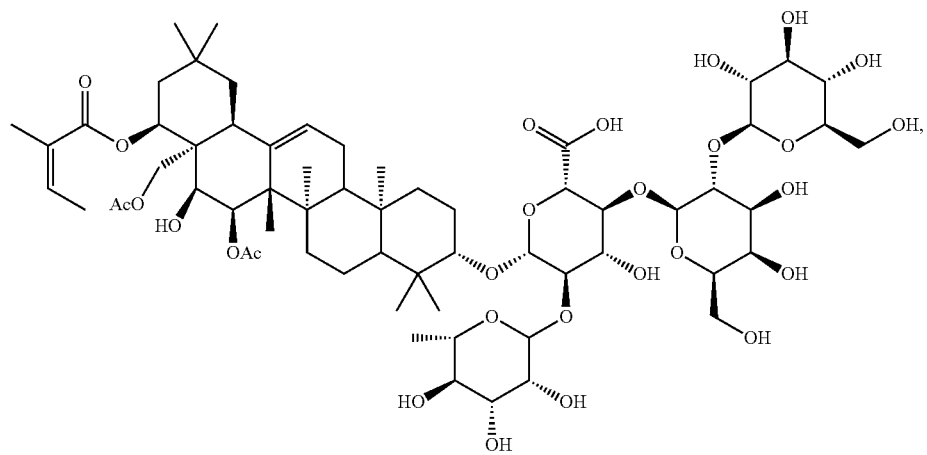

or a pharmaceutically acceptable salt thereof.

In yet a further aspect, the invention provides methods for treating a fungal infection in a subject. The methods include administering to the subject a compound of Formula III:

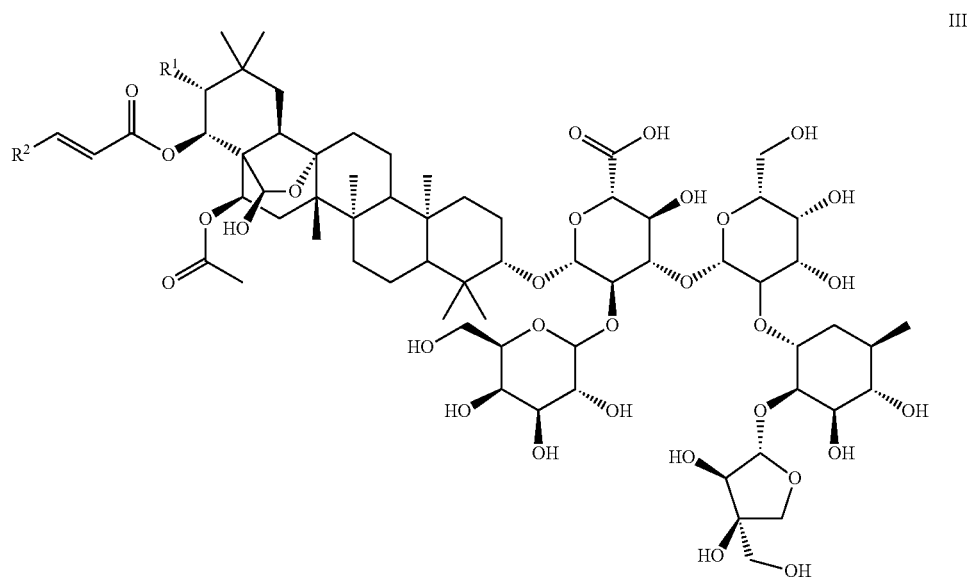

III or a pharmaceutically acceptable salt thereof, wherein:

$R^1$ is H or $C(O)R^B$;
$R^2$ is $C_{1-6}$ alkyl or aryl; and
$R^B$ is $C_{2-6}$ alkenyl.

In some embodiments, the compound is:
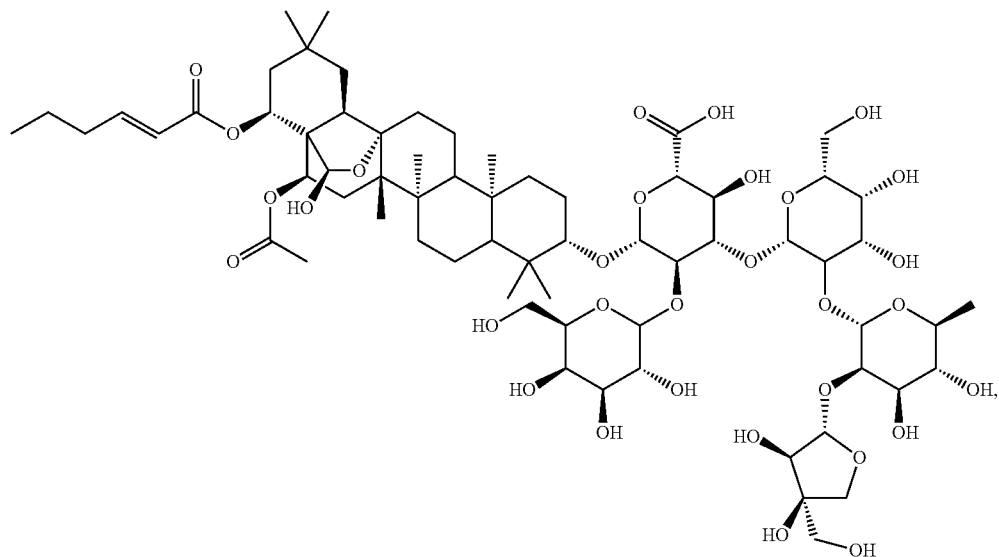
30
or a pharmaceutically acceptable salt thereof.
In some embodiments, the compound is:
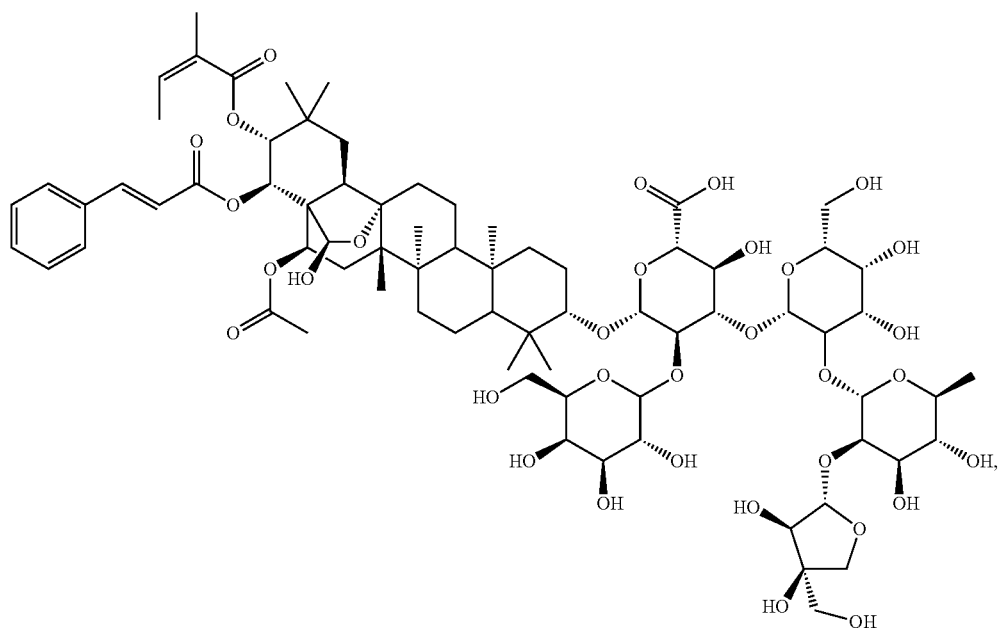
or a pharmaceutically acceptable salt thereof.
In yet another aspect, the invention provides methods for treating a fungal infection in a subject. The methods include administering to the subject a compound:

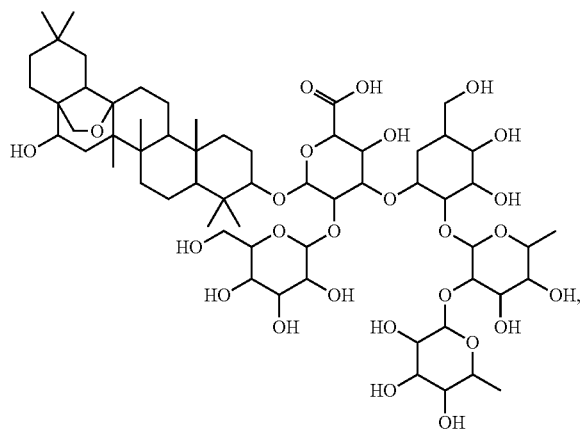

or a pharmaceutically acceptable salt thereof.

Also provided herein is the saponins described herein for use in the treatment of a fungal infection, and/or in the manufacture of a medicament for the treatment of a fungal infection.

In some embodiments of the methods described herein, the fungal infection is infection with a *Candida* species fungus, e.g., *C. albicans*.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

A compound screen to identify potential antifungal natural products was undertaken, identifying 12 saponins, some of which have not been previously described. This class of amphipathic natural products was represented by members of the maesabalide and barrigenol families, as well as others. In the *Caenorhabditis elegans* model, some saponins conferred nematode survival comparable to amphotericin B. Of the 12 antifungal saponins identified, two were selected for further analysis. *C. albicans* isolates were inhibited by these compounds at relatively low concentrations (16 and 32 μg/mL) including isolates resistant to clinically used antifungal agents. *C. albicans* hyphae and biofilm formation were also disrupted in the presence of these natural products, and studies demonstrate that fungal cells in the presence of saponins are more susceptible to salt induced osmotic stress. Although saponins are known for their hemolytic activity, we observed no hemolysis of erythrocytes at three times the minimal inhibitory concentration (100 μg/mL) for *C. albicans*, suggesting the saponins may have a preference for binding to fungal ergosterol when compared to cholesterol. Importantly, when used in combination with photosensitizer compounds, the fungus displayed increased susceptibility to photodynamic inactivation due to the ability of the saponins to increase cell permeability facilitating penetration of the photosensitizers. The large proportion of compounds identified as antifungal agents containing saponin structural features suggests it may be a suitable chemical scaffold for a new generation of antifungal compounds.

Figure 6A:
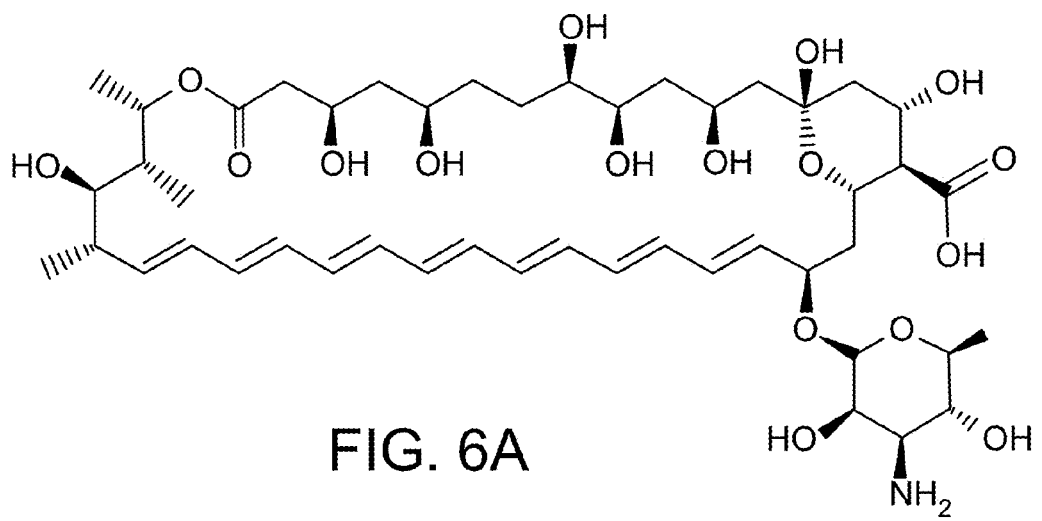
FIGS. 6A-B are the structures of two clinically relevant antifungal agents. 6A, The polyene antifungal amphotericin B; 6B, caspofungin, a member of the echinocandin antifungal family.
Figure 6B:
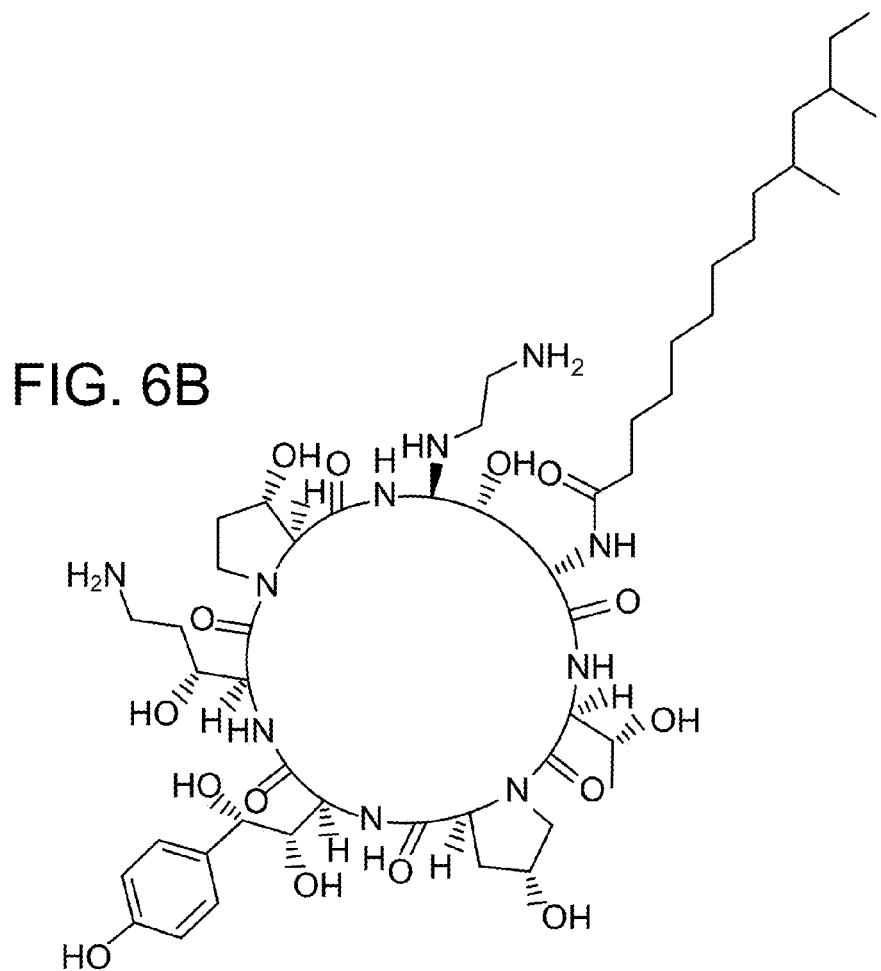

There is an urgent need for the development of new antifungal agents [reviewed in Spanakis et al., Clin Infect Dis, 43:1060-1068 (2006)]. Traditionally, natural products have provided a plethora of antimicrobial compounds. In particular, a current drug of choice for treatment of systemic candidiasis is the polyene amphotericin B (FIG. 6, panel a) originally isolated from *Streptomyces nodosus* Trejo (Gold et al., Antibiotics Ann, 1955-1956, 579-586; Trejo et al., J Bacteriol, 85:436-439 (1963)). Plants are also well known to produce a diverse array of natural products which harbor antimicrobial activity (Dixon, Nature, 411:843-847 (2001)), including phytoalexins and saponins.

Saponins

Saponins have been identified in over one hundred plant families and can be an integral part of the plant's defense mechanism. These natural products are composed of sugar moieties connected to a hydrophobic aglycone backbone. Various side chains to both the aglycone and the pendant sugar moieties create additional structural diversity. Saponins are able to form pores in lipid bilayers and are known to increase cellular permeability allowing uptake of molecules that would otherwise be excluded. In this report we utilized the nematode *Caenorhabditis elegans* as a heterologous host to screen a library of natural products (Breger et al., PLoS Pathog, 3:e18 (2007); Okoli et al., PLoS ONE, 4:e7025 (2009)), ultimately identifying twelve saponins which increased nematode survival. Some saponins were able to prolong nematode survival in a dose-dependent manner and further characterization of the antifungal activity of members of the saponin family demonstrate they can impede *C. albicans* biofilm formation and dramatically potentiate photodynamic inactivation (PDI) when coupled with photosensitizers (PSs) and harmless visible light. These compounds may be antifungal agents for clinical use either by themselves, or in conjunction with currently used antifungal agents.

Methods of Treatment

The methods described herein include methods for the treatment of disorders associated with fungal infections, e.g., infections with *Candida albicans*. Generally, the methods include administering a therapeutically effective amount of a therapeutic saponin compound as described herein, to a subject who is in need of, or who has been determined to be in need of, such treatment.

As used in this context, to "treat" means to ameliorate at least one symptom of the disorder associated with a fungal infections. Often, a fungal infections results in redness, itching. Discharge, and/or discomfort; thus, a treatment can result in a reduction in a reduction in redness, itching, discharge, and/or discomfort. Administration of a therapeutically effective amount of a compound described herein for the treatment of a condition associated with fungal infections will result in decreased levels of fungal organism present, and a reduction in symptoms if present.

Candidiasis

In some embodiments, the disorder is Candidiasis, e.g., oral thrush, vaginitis, or systemic candidiasis, e.g., candidemia. Most *candida* infections are minor and result in minimal complications such as redness, itching and discomfort, though the infections can be severe or even fatal if left untreated in certain populations, such as in immunocompetent persons. Candidiasis is usually a localized infection, e.g., of the skin or mucosal membranes, e.g., the oral cavity, the pharynx or esophagus, the gastrointestinal tract, the urinary bladder, or the genitalia. Walsh and Dixon, "Deep Mycoses," in Baron et al. eds. *Baron's Medical Microbiology* (4th ed.). Univ of Texas Medical Branch (1996).

In immunocompromised patients, *Candida* infections can affect the esophagus with the potential of becoming systemic, causing the much more serious fungemia called candidemia Immunocompromised patients include those with metabolic illnesses such as diabetes, or with weakened or undeveloped immune systems; diseases or conditions linked to candidiasis include HTV/AIDS, mononucleosis, cancer treatments, steroids, stress, and nutrient deficiency.

Diagnosis of *Candida* infections can be done using methods known in the art, e.g., via microscopic examination or culturing a sample suspected of containing the infections organism.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions and Methods of Administration

The methods described herein include the manufacture and use of pharmaceutical compositions, which include saponins described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., other anti-fungal agents.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, vaginal and rectal administration.

Methods of formulating suitable pharmaceutical compositions are known in the art, see, e.g., the books in the series *Drugs and the Pharmaceutical Sciences: a Series of Textbooks and Monographs* (Dekker, N.Y.). For example, solutions or suspensions used for parenteral, intradermal, vaginal or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery; in a crème or solid form for vaginal delivery; or in liquid form for use as a douche.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Combination Treatments

The methods described herein can also include the administration of a saponin compound described herein in combination with a therapeutic or sub-therapeutic dose of another antimycotic, e.g., clotrimazole, nystatin, fluconazole, and ketoconazole. In severe infections (e.g., in hospitalized patients), amphotericin B, caspofungin, Gentian violet, or voriconazole may be used in combination with the compounds described herein.

EXAMPLES

The invention is further described in the following examples, which do not limit the scope of the invention described in the claims.

Example 1

Identification of Antifungal Compounds

The ability of pathogenic fungi to overcome antifungal agents in clinical use has created a need to develop new antifungal compounds. To facilitate drug discovery and overcome drug development hurdles, such as toxicity and solubility, a high-throughput whole animal assay for the identification of compounds with antifungal efficacy has been developed using the nematode *C. elegans* as a heterologous host (Breger et al., PLoS Pathog, 3:e18 (2007); Okoli et al., PLoS ONE, 4:e7025 (2009)).

The procedure for the co-inoculation antifungal compound screen were conducted as previously described (Okoli et al., PLoS ONE, 4:e7025 (2009); Tampakakis et al., Nat Protocols, 3:1925-1931 (2008)), using the *C. albicans* strain DAY185 (Davis et al., Infect Immun, 68:5953-5959 (2000)) and the *C. elegans* glp-4; sek-1 double mutant.

The determination of the lowest concentration of the selected compounds showing in vitro antifungal activity was accomplished by following the steps detailed in the co-inoculation assay, using two-fold serial dilutions of the test compounds. The wells were assessed by visually monitoring the turbidity for concentrations exhibiting in vitro inhibition of *C. albicans* growth.

This assay allows simultaneous assessment of a compound's potential toxicity and the ability to promote the survival of the nematode in the presence of *C. albicans*, including modes of action not traditionally considered in antifungal assays such as impeding a fungal virulence factor or promoting host immune response. We performed a screen of 2,560 natural products representing a fraction of the Analyiticon Discovery compound collection (ac-discovery.com) housed at the Broad Institute of Harvard and MIT (Cambridge, Mass.). Through this screen we found that most of our hits, defined as conferring survival to at least 20% of the nematodes after five days, were from the saponin family of natural compounds. These natural products identified in the primary screen were retested and confirmed (FIG. 1; Table 1). Of the twelve saponins identified, six of the compounds (A7, A8, A24, A20, A17, and A21) had no precedent in the literature regarding their structure or biological activity, however in some cases related analogs have been described. Moreover, although the antifungal effects of some of these saponins have been reported (Sata et al., Biosci Biotechnol Biochem, 62:1904-1911 (1998); Ohtani et al., Phytochem, 33:83-86 (1993)), their efficacy against *Candida* spp. has not been studied.

TABLE 1

Minimal inhibitory concentrations (MIC) in vitro and effective concentration ($EC_{50}$) in vivo of saponins identified in the *C. elegans-C. albicans* screen.*

| | Saponin natural products | MIC in vitro (μg/mL) | $EC_{50}$ in vivo (μg/mL) |
|---|---|---|---|
| | Amphotericin B | 1.0 | 2.0 |
| A2 | Sakurasosaponin | 27.5 | 55.1 |
| A8 | | 5.8 | 23.1 |
| A16 | Aginoside | 47.0 | 47.0 |
| A24 | | 13.3 | 13.3 |
| A11 | | 38.9 | 38.9 |
| A20 | | 4.8 | 4.8 |
| A7 | | 3.1 | 3.1 |
| A19 | | 26.5 | 26.5 |
| A25 | | 28.7 | 28.7 |
| A17 | | 31.0 | 31.0 |
| A21 | | 16.5 | 16.5 |

*Compound A6 (Arvensoside B) was unable to provide a MIC or $EC_{50}$ due to the limited antifungal activity of the compound.

After confirmation of these hits, dose response experiments were conducted to determine the concentration that provided maximum nematode survival. The compounds conferred a range of nematode survival from 27% (compound A6) to 93% (compounds A2, A7, A24, and A25), however, with the exception of A6, all compounds conferred a nematode survival over 65% (FIG. 1).

Several representative members of the saponin family of natural products (compounds A8, A11, A16, A20, and A24; FIG. 1) had similar chemical structures and conferred a high degree of worm survival (FIG. 1). Compounds A8 and A24 are closely related analogs to the known antifungal natural product aginoside (A16) (Sata et al., Biosci Biotechnol Biochem, 62:1904-1911 (1998); Carotenuto et al., Phytochem, 51:1077-1082 (1999)). As shown in FIG. 1, A8 is the C-2 des-hydroxy analog of aginoside, and the similar activities of A8 and A16 suggests that the C-2 oxygenation state does not affect the overall antifungal activity. The pentasaccacharide A24 differs from aginoside through the addition of the β-D-glucopyranose sidechain, and this additional glycoside did confer an increase in protection from 67-93% (FIG. 1). Similarly, compounds A11 and A20, which are both characterized by oxygenation state differences at the C-6 position in the aglycone backbone as well as differences in the appended sugar moieties when compared to A8, A16, and A24, also conferred protection to the worms (FIG. 1). Clearly, a range of glycoside substitutions is tolerated in this class of compounds and these differences do not appear to drive the overall activity. Notably, although members of the aginoside family of saponins are well documented in literature, there was no description of the two new glycosylated derivatives of aginoside, A8 and A24, or a report of their antifungal activity. It should be noted that there were several other structurally related analogs composed primarily of the aglycone backbone that were negative in the screen. Whether this is due to specific differences in their fungicidal activity or simply a reflection of their different physicochemical properties (e.g. solubility) is uncertain.

Figure 1A:
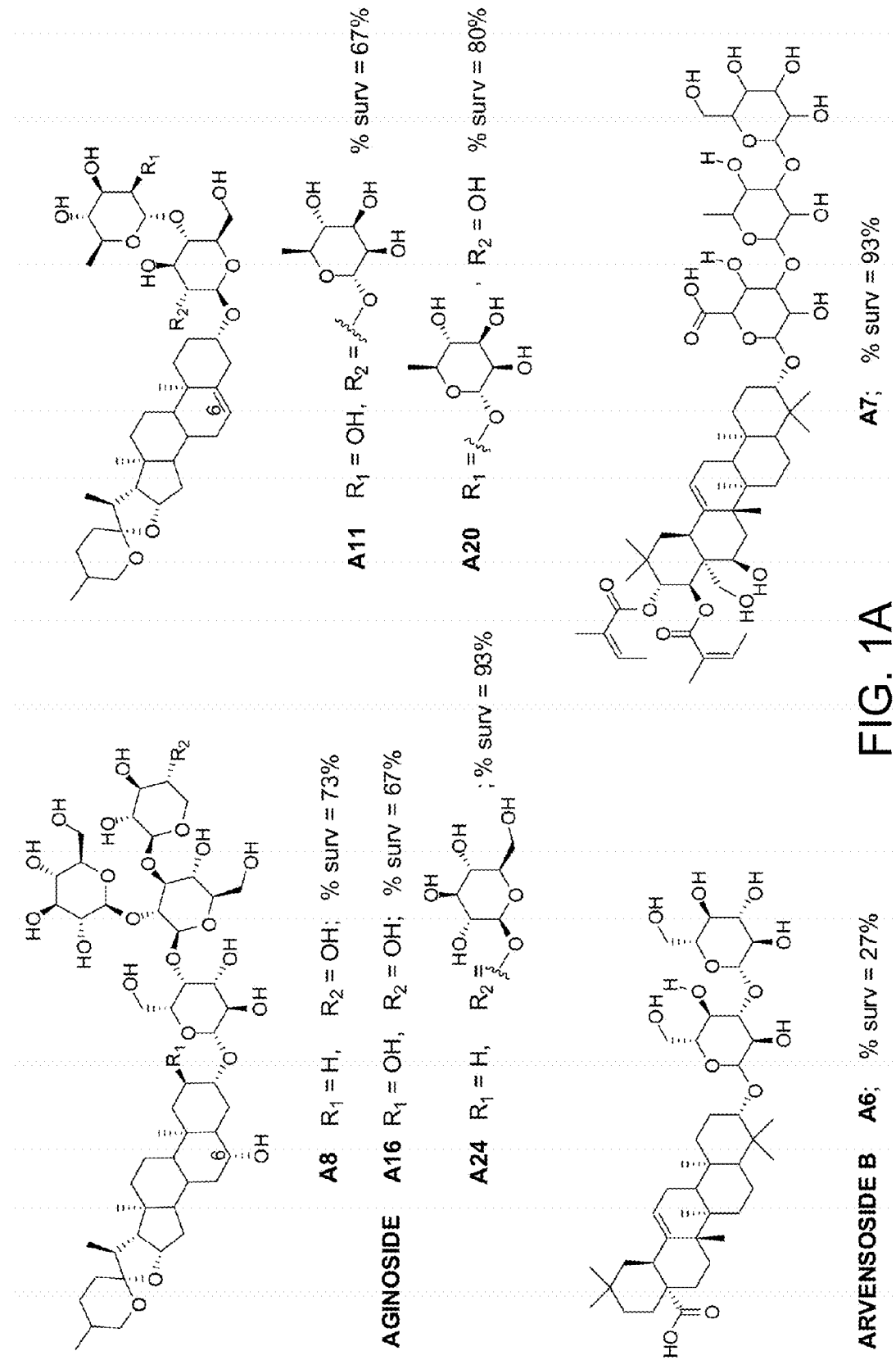
FIGS. 1A-C show structures of the natural product saponins identified in the *C. elegans*-*C. albicans* antifungal drug discovery screen (all structural representations were provided by Analyticon Discovery, Germany). For each of the compounds the maximum nematode survival (%) is indicated.
Figure 1B:
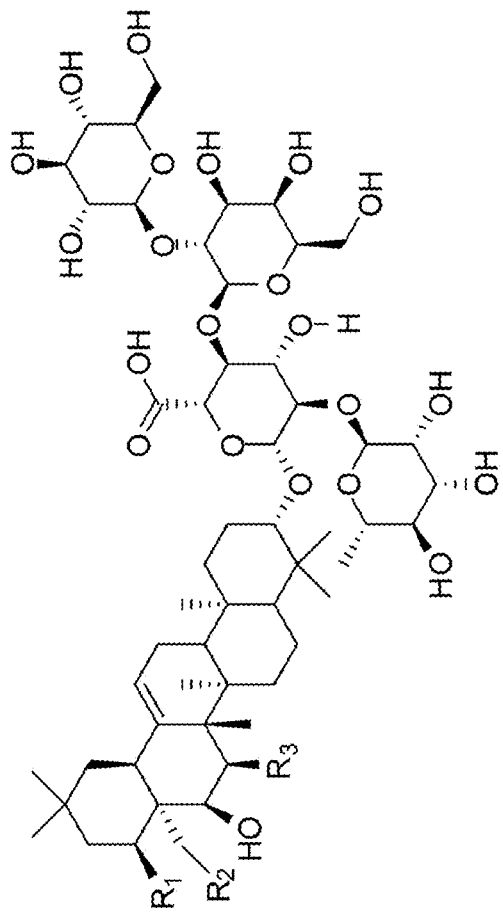
Figure 1B:
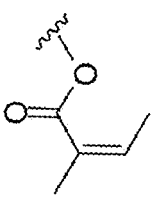
Figure 1B:
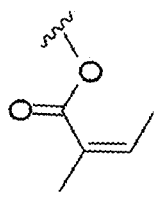
Figure 1C:
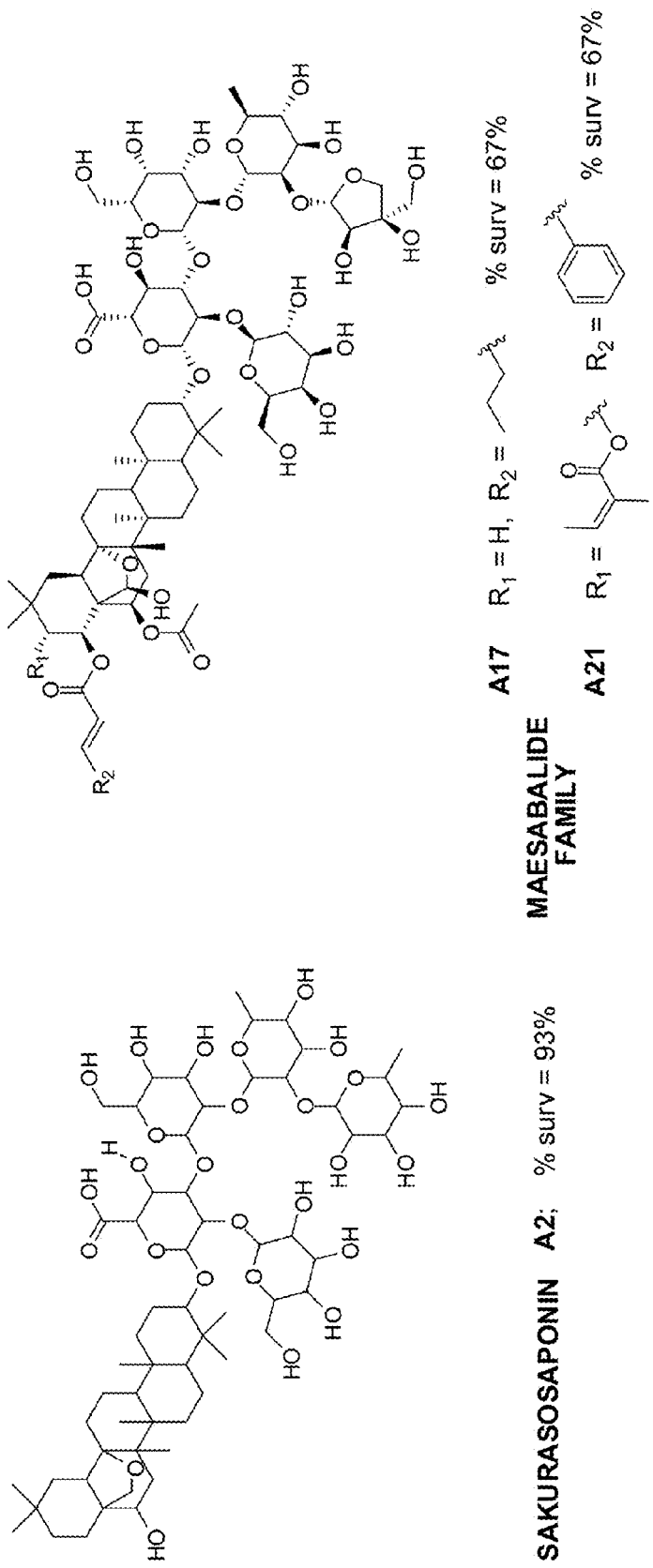
Figure 2A:
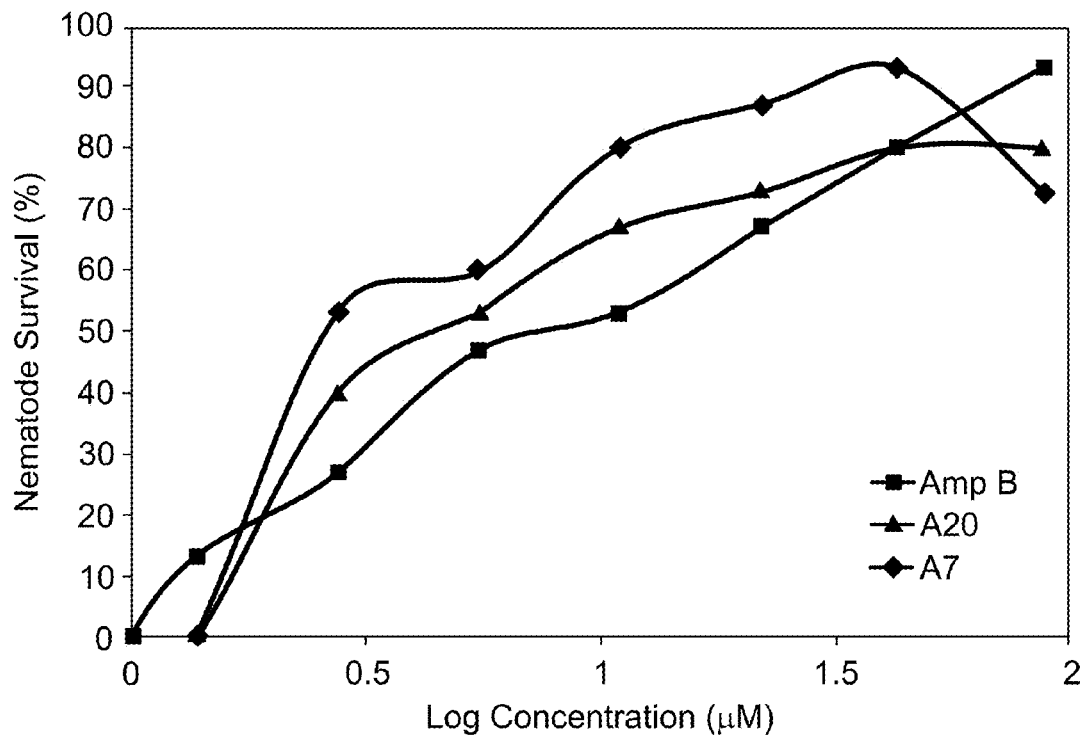
FIGS. 2A-B are line graphs showing the dose response of select compounds identified in the *C. elegans*-*C. albicans* assay. 2A, Two saponins (A7 and A20) were as effective as amphotericin B in promoting *C. elegans* survival. The decrease in nematode survival for A7 at the highest concentration tested suggests the saponin maybe toxic to the nematode 2B, Dose response of two saponin compounds (A16 and A19) used in further studies.
Figure 2B:
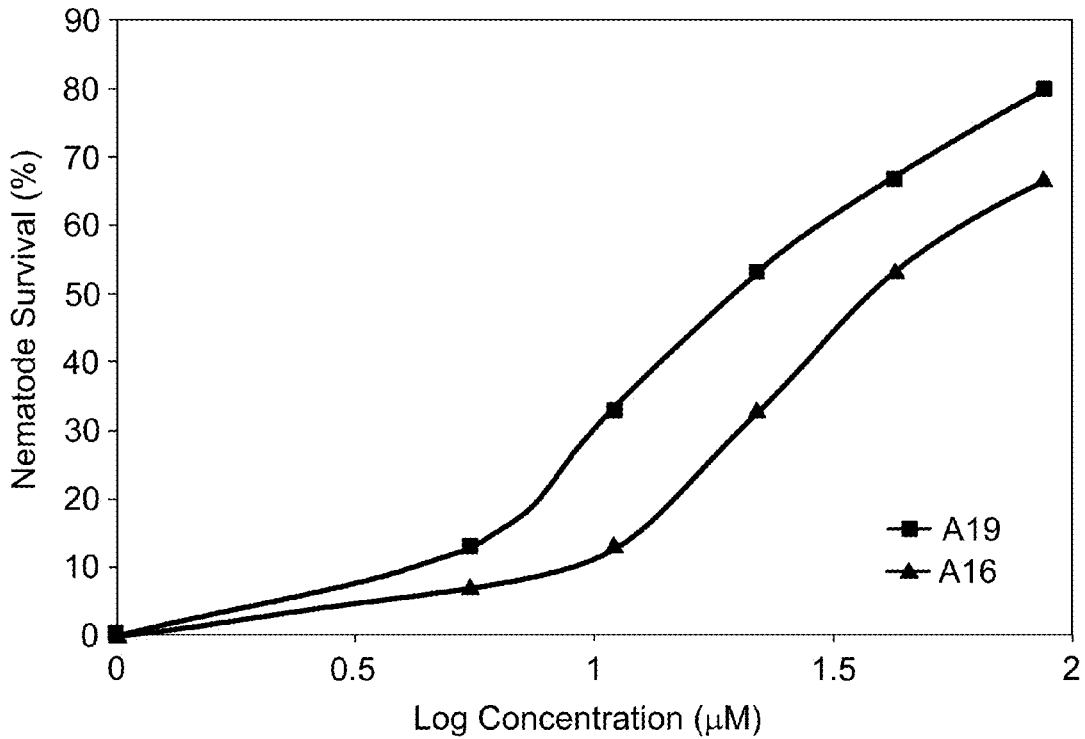

Six polyglycosylated saponins were identified in the screen (A2, A7, A17, A19, A21, and A25) that completely inhibited in vitro growth of *C. albicans* and provided excellent protection to the worms (FIG. 1, Table 1). Interestingly, several of these saponins were able to confer a level of protection similar to that provided by amphotericin B (93%, Table 1) (Okoli et al., PLoS ONE, 4:e7025 (2009)), the current clinical antifungal agent of choice for systemic candidasis. Of particular interest, compound A7 was able to extend *C. albicans*-infected nematode survival to a similar level as amphotericin B, however only half of the concentration of A7 was required (FIG. 2, panel a). There were no previous reports in the literature describing the structure of compound A7. Unfortunately, at high concentrations it appears that compound A7 is toxic to the nematode (FIG. 2, panel a), although there does appear to be a therapeutic window, and modification of the compound might reduce its toxicity. Compound A2 is the known natural product sakurasosaponin, and its antifungal properties have been previously reported by Ohtari et al. (Ohtani et al., Phytochem, 33:83-86 (1993)). Compounds A17 and A21, which share a similar aglycone, are related to the maesabalide family of compounds; however, there were no reports for these unique pentasaccarides that incorporate the distal furanose residue or reports of their antifungal activity (Germonprez et al., J Med Chem, 48:32-37 (2005)). Compounds A19 and A25 also demonstrated excellent in vitro activity completely inhibiting *C. albicans* growth and providing excellent nematode protection (FIG. 1; FIG. 2, panel b; Table 1). These saponins share a similar aglycone core which is related to the barrigenol family of natural products, however, there are scant reports for compounds displaying this arrangement of polyglycosylation (Herlt et al., J Nat Prod, 65:115-120 (2002)). There is one report in the literature for compounds closely related to A19 (Liu et al., Chinese Chem Lett, 17: 211-214 (2006)) and no references were found for compound A25. While similar compounds have reported insect antifeedant properties (Herlt et al., J Nat Prod, 65:115-120 (2002)), there was no description of their antifungal properties and, based on the potent inhibition and excellent protective effects, we feel this class of compounds may offer unique opportunities to discover novel compounds with improved activity or inhibit novel fungal biological pathways. Collectively, the relatively "soft" structure activity relationship (SAR) demonstrated by most the saponins is encouraging, as these compounds retained excellent antifungal potency even though there are a variety of aglycones, glycosides, and glycosidic linkages displayed between them.

The dose response experiments also allow the estimation of the in vitro efficacy of these compounds against *C. albicans* and the effective dose that resulted in 50% survival of the nematodes ($EC_{50}$) was determined for these 12 natural products (Table 1). Comparison of the concentrations of both the minimal inhibitory concentration (MIC) and $EC_{50}$ can provide insight into possible actions the compound may have on the fungus. Compounds with a lower or equal $EC_{50}$ when compared to the MIC suggest the compounds have higher efficacy during the infection process. This could result from several factors including 1) immuno-modulatory effects from the compounds, 2) inhibition of virulence factors, or 3) desirable solubility and/or permeability properties of the saponins resulting in the compounds reaching the target site effectively. Of note is that previous studies showed the nematode $EC_{50}$ concentrations of known antifungal compounds are higher than the concentrations needed for in vitro efficacy (for example the MIC for several azoles in clinical use and amphotericin B were half the concentration required to confer 50% nematode survival (Table 1; (Okoli et al., PLoS ONE, 4:e7025 (2009)). However, the saponins had identical $EC_{50}$ and MIC concentrations, with the exception of compounds A2 and A8 (Table 1), suggesting their in vivo antifungal activity may also be derived by alternative mechanisms.

One explanation for the similarity in the $EC_{50}$ and MIC concentrations is that the saponins may possibly alter the nematode immune response. Previous studies have demonstrated that saponins have a stimulatory affect on the Th1 immune response and production of cytotoxic T-lymphocytes, which has lead to their use as adjuvants in vaccines (Sun et al., Vaccine, 27:1787-1796 (2009)). It is unclear how saponins alter this immune response, although a correlation between the length of the sugar side chain and the increase in immune stimulating ability has been observed, where the longer the sugar moiety, the greater IgG antibody response (Sun et al., Vaccine, 27:1787-1796 (2009)). It should be noted that eleven of the twelve saponins identified in the screen have at least three sugars attached (FIG. 1). Although *C. elegans* does not have an adaptive immune response and it is currently unclear if the immune response of the nematode is altered in the presence of these compounds, other studies have shown saponins induce innate immune responses; production of cytokines, such as interleukins and interferons, is increased by saponins which may lead to stimulation of the immune system (Francis et al., British Journal of Nutrition, 88:587-605 (2002)).

Example 2

Further Characterization of Two Identified Natural Products

Two of these identified natural products (one from each group), A16 (aginoside) and A19, were selected for further studies based on the following considerations: (1) none of the concentrations used in the dose response experiment showed signs of toxicity to the worms (FIG. 2, panel b); (2) the compounds showed a high percentage of protection to the worms (67% and 80% respectively) and related structural analogs from each class conferred the highest protection observed, 93% (A24 and A25) (FIG. 1); and (3) the compounds were readily available from the vendor (Analyticon Discovery, Germany). Dose response experiments for A16 and A19 demonstrated dose-dependent nematode survival to *C. albicans* infection up to the maximum concentration tested for the compounds (94 μg/mL for A16 and 106 μg/mL for A19; FIG. 2, panel b). Using the standard Clinical and Laboratory Standards Institute (CLSI) procedure, the in vitro MIC of these two compounds was determined on the following *C. albicans* strains: DAY185 (the standard strain used throughout the screen), two fluconazole-resistant strains of *C. albicans*, and an echinocandin-resistant strain of *C. albicans* (Table 2). Compounds A16 and A19 had identical MIC values for the *C. albicans* isolates tested, regardless of resistance mechanisms to clinically used antifungal agents. These findings indicate that the molecular mechanisms of *C. albicans* which confer resistance to antifungal agents in current clinical use do not provide cross-resistance to the natural products identified in this screen in agreement with other studies (Zhang et al., Biol Pharm Bull, 28:2211-2215 (2005)). Importantly, the natural products are likely to have a different mode of action than members of the triazole and echinocandin family, and may be effective in treatment for isolates resistant to conventional antifungal compounds.

TABLE 2

The MIC results of clinically relevant compounds and two identified natural products on *C. albicans*.*

| Strains | Fluconazole | Caspofungin | Amphotericin B | A16 | A19 |
| --- | --- | --- | --- | --- | --- |
| *C. albicans* strains | | | | | |
| DAY185 | 2 | 2 | 2 | 16 | 32 |
| Fluconazole-resistant strains | | | | | |
| 98-145 | >128 | 1 | 2 | 16 | 32 |
| 95-120 | 32 | 1 | 2 | 16 | 32 |
| Echinocandin-resistant strain | | | | | |
| A15 | 2 | 8 | 2 | 16 | 16 |

*MIC concentrations are presented in μg/mL

Because of the significance of biofilm in human disease (for example, biofilm formation on medical devices is associated with increased resistance to antifungal agents (Blankenship et al., Curr Opin Microbiol, 9:588-594 (2006); d'Enfert, Curr Drug Targets, 7: 465-470 (2006); Kumamoto, Curr Opin Microbiol, 5:608-611 (2002)) we studied the effects of saponins on *Candida* biofilms.

The minimal inhibitory concentration (MTC) was determined for strains DAY185, 98-145, 95-120 (White et al., Antimicrob Agents Chemother, 46:1704-1713 (2002)), and A15-10 (Garcia-Effron et al., Antimicrob Agents Chemother, 53:112-122 (2009)) spectrophotometricially using RPMI 1640 media (Mediatech, Inc.) following the standard CLSI microdilution protocol M27-A (National Committee for Clinical Laboratory Standards, Reference method for broth dilution susceptibility testing of yeasts. Tentative standard M27-A, Villanova, Pa. (1995)). Biofilm assays using identified compounds were conducted as previously described (Richard et al., Eukaryot Cell, 4:1493-1502 (2005)). The biofilm dry mass was determined by drying the silicone squares in a chemical hood, and weighing the resulting biofilm mass subtracting the previously weighed mass of the silicone square. Biofilm pictures were captured using a confocal laser microscope (TCS NT, Leica Microsystems). Cells were grown at 30° C., exposed to PS for 30 min, and then washed with PBS. Cells were observed for PS localization by confocal laser microscopy (TCS; NT Leica) as described previously (Fuchs et al., Antimicrob Agents Chemother, 51:2929-2936 (2007)).

Caspofungin (Merck) served as a known antifungal compound control. In vitro hyphal inhibition was assessed by incubation of DAY185 in RPMI 1640 media at 37° C. After 48 hours the cultures were visually inspected for hyphal formation by microscopy. The ability of the antifungal compound A16, at either 2 or 4 μg/mL, to induce osmotic stress was assessed using DAY185 grown in a 96 well microtiter plate containing RPMI 1640 media and NaCl, ranging in concentrations from 0-2 M in 0.25 M increments. The growth of the fungus was measured spectrophotometricially after 48 hours of growth at 35° C.

Figure 3:
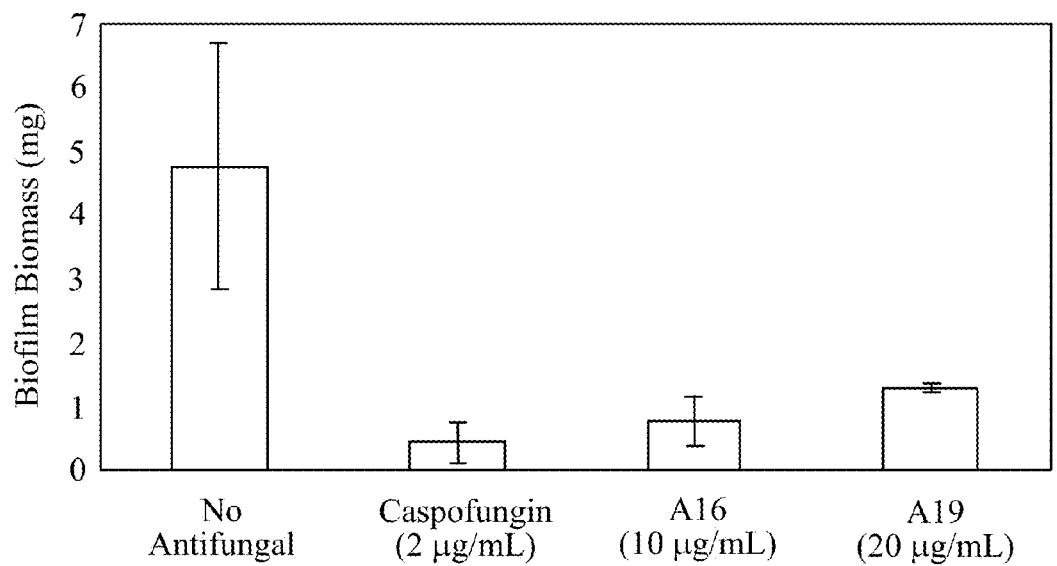
FIG. 3 is a bar graph showing biofilm formation for two saponin family members identified in the screen compared to untreated silicone pads and caspofungin, a compound able to inhibit *C. albicans* biofilm formation. Standard deviations are depicted and based on 5-11 silicone pad measurements.

Both A16 and A19 were able to inhibit biofilm formation at concentrations below the MIC (10 and 20 μg/mL for A16 and A19, respectively) to a level comparable with the echinocandin caspofungin (FIG. 3). With the exception of the echinocandidns, most currently used antifungal agents are unable to inhibit biofilm formation to a significant degree.

C. albicans biofilms are composed of hyphae, pseudohyphae, yeast cells, and an extracellular matrix, where the hyphae play an integral role within this complex. In order to address the reduction in biofilm formation in the presence of saponins, we tested the ability of compound A16 to inhibit hyphae formation at various concentrations in RPMI. Untreated C. albicans is able to form extensive hyphal networks, however when C. albicans is incubated with A16 at 2 μg/mL there are very few hyphae formed and are much smaller in size (~5-7 cells in length). When treated with 1 μg/mL of A16 there is a visible reduction in the number of hyphae, and the culture primarily consists of pseudohyphae and yeast cells.

Example 3

Hemolysis Studies

Representatives of the saponins family are able to disrupt cellular membranes and the lytic activity on erythrocytes has been used as an assay for some saponins Francis et al., British Journal of Nutrition, 88:587-605 (2002)). This property is derived from the affinity of some saponins for binding cholesterol forming insoluble pores composed of the sterol and saponins (Bangham et al., Nature, 196:952-953 (1962); Glauert et al., Nature, 196:953-955 (1962)). Although the hemolytic properties of saponins have been well documented, several saponins are now known to have little or no hemolytic activity (Sun et al., Vaccine, 27:1787-1796 (2009); Francis et al., British Journal of Nutrition, 88:587-605 (2002)). The dose-response experiments previously used to determine the $EC_{50}$ and approximate the MIC can also indicate if the saponins maybe toxic to C. elegans and potentially to mammalian cells. The compound may potentially be toxic to the nematode if a decrease in C. elegans survival is observed despite an increase in the concentration of the compound.

The cytotoxicity for the identified compounds was confirmed as previously described (Breger et al., PLoS Pathog, 3:e18 (2007); Moy et al., Proc Natl Acad Sci USA, 103: 10414-10419 (2006)). Hemolysis of sheep erythrocytes (Rockland Immunochemicals) was monitored on a spectrophotometer at $A_{540}$ with the two natural products A16 and A19 (100 μg/mL) in 2% DMSO. Triton X-100 and DMSO were used as controls.

Of the 12 saponins conferring an increase in C. elegans survival, only A7 and A24 displayed a decrease in nematode survival when tested at higher concentrations (FIG. 2, panel a; data not shown). This trend suggests the saponins could be toxic at high concentrations, although both were able to confer 93% nematode survival at a lower concentration. The in vivo nature of this antifungal discovery assay may have limited the number of toxic saponins identified in the screen, as they may have been toxic to the nematode during the screening process. Importantly, hemolysis experiments using sheep erythrocytes and the two purchased saponins (A16 and A19) demonstrated no hemolytic activity at 100 μg/mL, a concentration which is at least three times the MIC for C. albicans DAY185.

The aglycone backbone of saponins is believed to play a role in hemolysis as this core has an affinity for cholesterol (Glauert et al., Nature, 196:953-955 (1962)). The saponin aglycone structure can be divided into the triterpenoid and steroidal structural subclasses (Sparg et al., J Ethnopharmacol, 94:219-243 (2004)), where steroidal saponins have higher hemolytic activity and hemolysis occurs at a faster rate when compared to triterpenoid saponins (Takechi et al., Planta Med, 61:76-77 (1995)). All 12 compounds identified in the assay were triterpenoid based saponins and may explain why only two compounds displayed potential toxicity in C. elegans. Other studies have suggested the hemolytic properties of saponins could be due to several factors including the types of side chains and the number of appended glycosides and polar functional groups present in the aglycone (Francis et al., British Journal of Nutrition, 88:587-605 (2002)). Compound A24 was the only compound in this group that showed evidence of toxicity to the worms at concentrations >27 μg/mL, suggesting that while the antifungal activity is relatively conserved with a range of glycoside substitution patterns, toxicity may be related to the differences in pendant sugar moieties rather than the core triterpenoid aglycone.

Example 4

Osmotic Stress and Potentiation of Photodynamic Inactivation in C. albicans by A16

Some saponins are capable of forming pores in Saccharomyces cerevisiae membranes by binding to the fungal sterol ergosterol causing cellular leakage (Simons et al., Antimicrob Agents Chemother, 50:2732-2740 (2006)). To investigate if these saponins increase cellular leakage and permeability, the potential of compound A16 to increase the susceptibility of the fungus to osmotic stress and enhance photodynamic inactivation (PDI) was assessed.

The PS used were Rose Bengal (RB, Sigma-Aldrich, St. Louis, Mo.) and chlorin(e6) (ce6, Frontier Scientific, Logan, Utah). PEI-ce6 was synthesized as a covalent conjugate between polyethylenimine (MW range 10,000-25,000, an average of one ce6 per chain) and ce6 as described previously (Tegos et al., Antimicrob Agents Chemother, 50:1402-1410 (2006)). Stock solutions were prepared in water at a concentration of 2 mM and stored for a maximum of 2 weeks in the dark at 4° C. before use. Spectra of stock solutions of PS diluted 140- to 280-fold in methanol were recorded. A non-coherent light source with interchangeable fiber bundles (LC122; LumaCare, London, United Kingdom) was employed. Thirty-nanometer-band-pass filters at ranges of 540±15 nm for RB, and 660±15 nm for ce6 and PEI-ce6 were used. The total power output from the fiber bundle ranged from 300 to 600 mW. The spot was arranged to give an irradiance of 100 mW/cm$^2$.

The statistical values for the PDI experiments represent the mean of three separate experiments, and bars presented in the graphs represent standard error from the mean. Differences between mean values were tested for significance by an unpaired two-tailed Student t test, assuming equal or unequal variations as appropriate. A P value of less than 0.05 indicated statistical significance.

The *C. albicans* cell wall and membrane are important for osmoregulation to maintain proper physiological conditions to carryout enzymatic reactions. Since saponins are able to disrupt the fungal cell membrane, external osmotic stress should also have detrimental effects on the fungal cell. *C. albicans* was grown in the presence of 2 μg/mL of compound A16 under various salt concentrations to assess the effect the saponin has on salt induced osmotic stress.

Fungal suspensions in phosphate-buffered saline (PBS) (initial concentration, $10^8$ CFU ml$^{-1}$) were pre-incubated with A16 for 1 and 24 hrs in combination with the appropriate PS in the dark at room temperature for 30 min at concentrations varying from 10 to 100 μM for the PS and 4 μg/ml for A16. The cell suspensions were centrifuged at 12,000 rpm, washed twice, and suspended in sterile PBS. The cell suspensions were placed in wells of 48-well microtiter plates (Fisher Scientific) and illuminated using appropriate optical parameters. Fluences ranged from 0 to 80 J/cm$^2$ at a fluence rate of 100 mW/cm$^2$. During illumination, aliquots of 100 μL were taken to determine the CFU. The contents of the wells were constantly stirred during illumination to ensure that cells did not settle to the bottom of the wells and mixed before sampling. The aliquots were serially diluted 10-fold in PBS and were streaked horizontally on square YPD agar plates as described (Jett et al., Biotechniques, 23:648-650 (1997)). Plates were incubated at 30° C. for 48 hrs. Two types of control conditions were used: illumination in the absence of PS or A16 and incubation with PS and A16 in the dark.

The fungus incubated with A16 was unable to grow at a high salt concentration when compared to the untreated control (0.5 M for the A16 treated versus 1.25 M for the untreated control) demonstrating an increased sensitivity to NaCl induced osmotic stress.

Figure 4A:
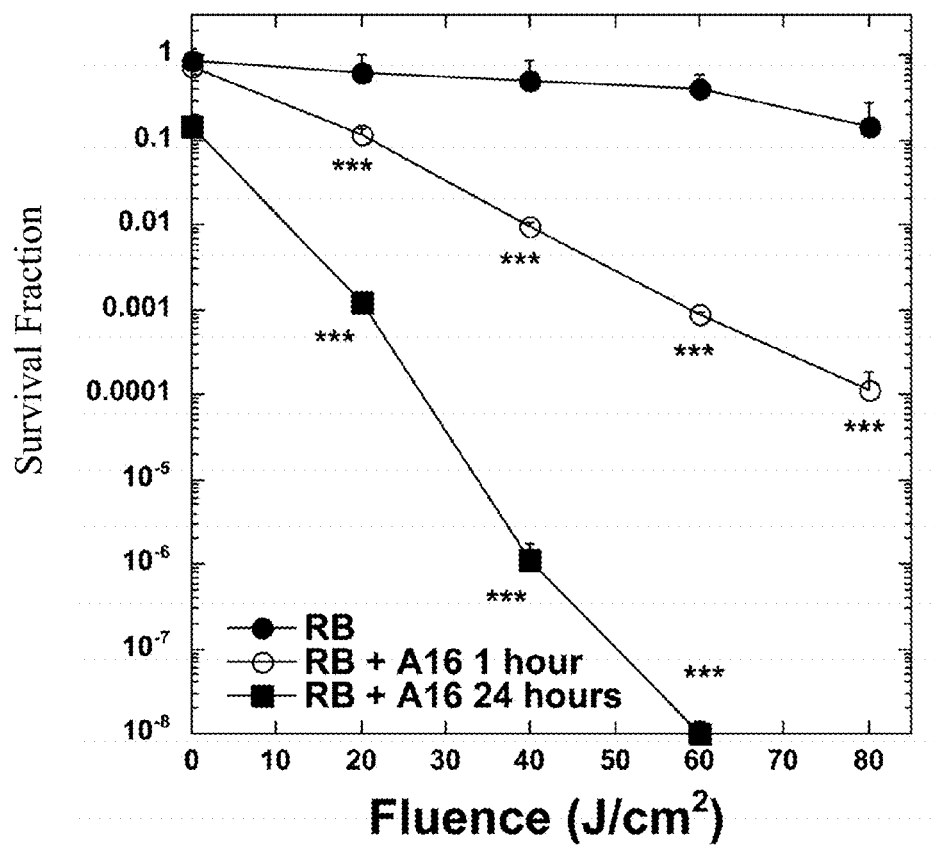
FIGS. 4A-C are line graphs showing phototoxicity in *C. albicans* DAY185 after incubation with or without 4 μg/ml A16 and (4A) 100 μM RB, (4B) 100 μM ce6, and (4C) 10 μM PEI-ce6. Fungal cells were incubated with the PS for 30 min, washed and then illuminated and survival fractions were determined as described in the methods. Values are means of three separate experiments and bars are SEM. *** P<0.001 compared to PS alone.
Figure 4B:
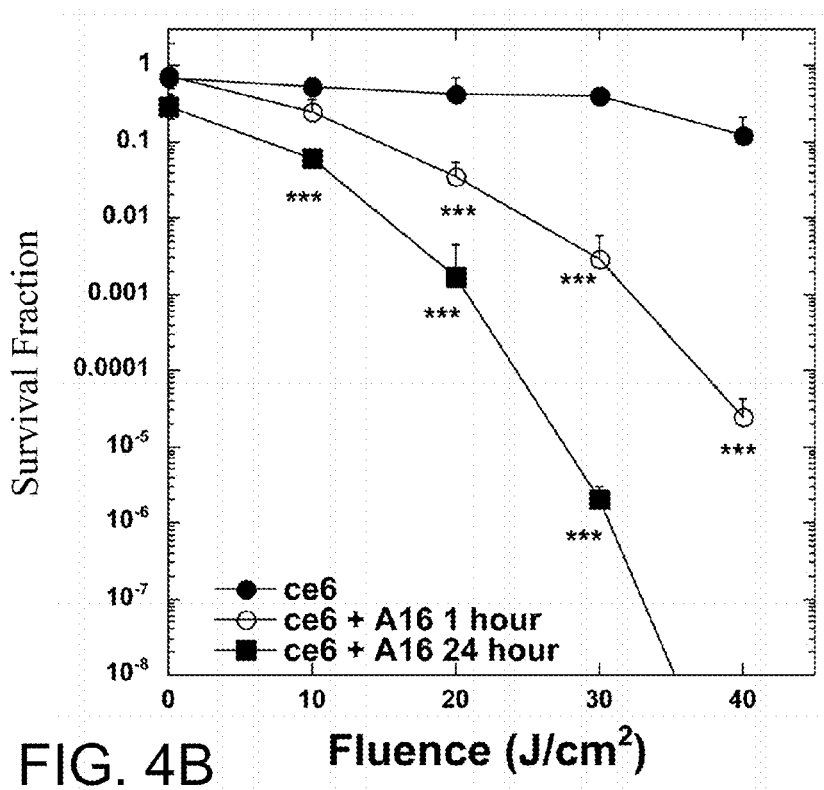
Figure 4C:
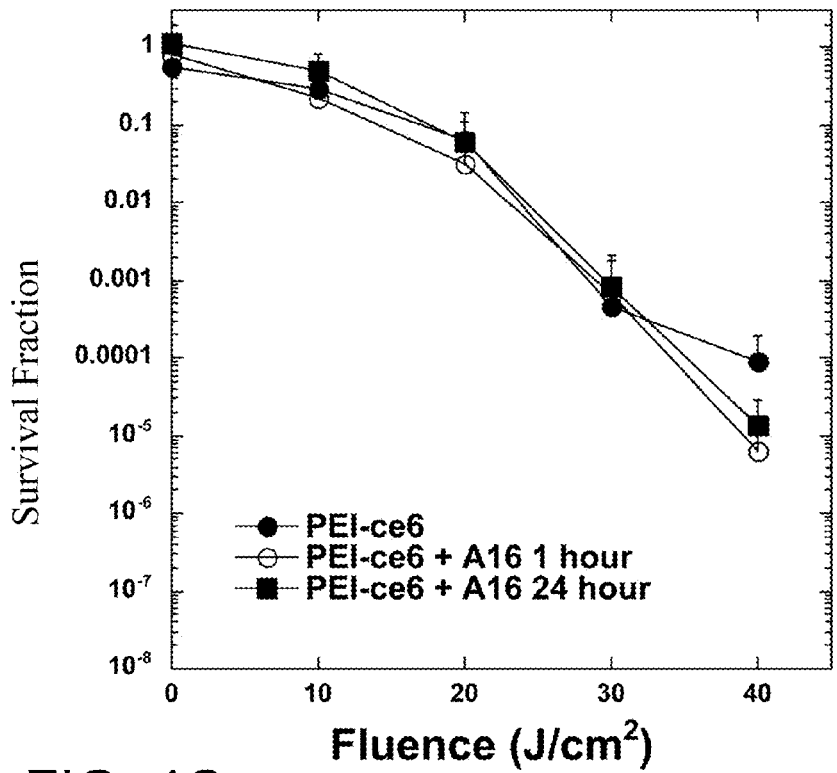
Figure 5A:
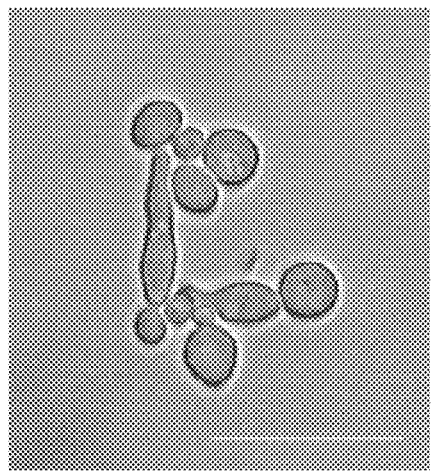
FIGS. 5A-D are confocal laser scanning microscope images of *C. albicans* cells after incubation with (5A) 100 μM ce6 and in combination with 4 μg/ml A16 for (5B) 1 hr and (5C) (5D) 24 hrs. Scale bar=20 μm for (5A), (5B), and (5C) and 14 μm for (5D).
Figure 5B:
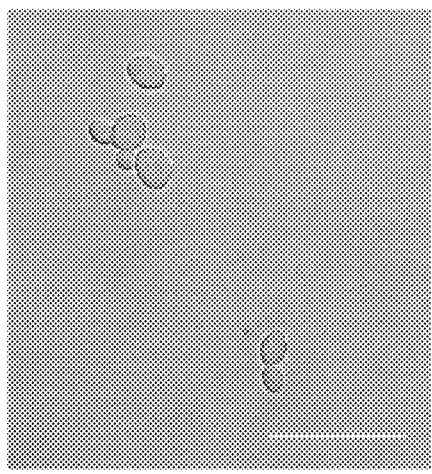
Figure 5C:
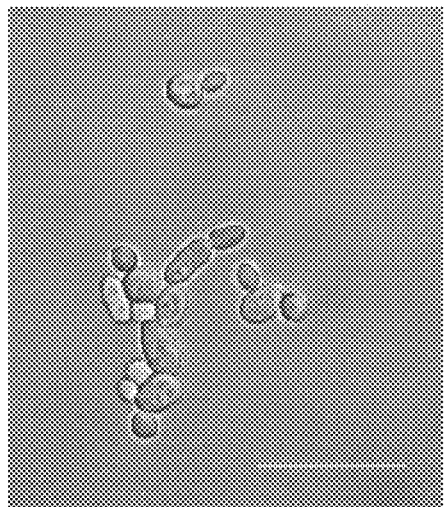
Figure 5D:
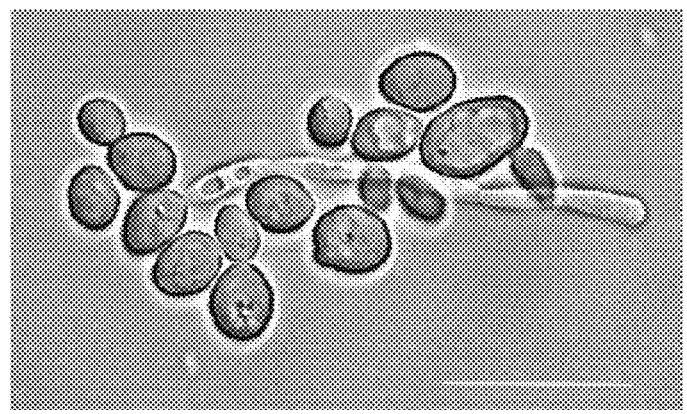

Photodynamic inactivation utilizes a non-toxic dye, or photosensitizer (PS), which is able to generate reactive oxygen species, such as singlet oxygen and hydroxyl radical, in the presence of oxygen and low-intensity light of the correct wavelength to be absorbed by the PS ultimately producing toxic effects in microbial cells (Fuchs et al., Antimicrob Agents Chemother, 51:2929-2936 (2007)). The application of PDI and photodynamic therapy (PDT) as an antimicrobial treatment is a developing area of photobiology and has been investigated as a highly promising potential treatment for localized infections (Demidova et al., Int J Immunopathol Pharmacol, 17: 245-254 (2004); Hamblin et al., Photochem Photobiol Sci, 3:436-450 (2004)). Three different PSs molecules were used for studies with compound A16: two were anionic, rose bengal (RB), chlorin(e6) (ce6), while the third was a polycationic conjugate of ce6 and polyethyleneimine (PEI-ce6). Both RB and ce6 are not taken up easily by yeast cells and at the concentrations used they had no statistically significant PDI effect (Fuchs et al., Antimicrob Agents Chemother, 51:2929-2936 (2007); Tegos et al., Antimicrob Agents Chemother, 50:196-203 (2006)). However, PEI-ce6 is more potent at lower concentrations than the other PS compounds against *C. albicans* and *C. neoformans* (Fuchs et al., Antimicrob Agents Chemother, 51:2929-2936 (2007); Tegos et al., Antimicrob Agents Chemother, 50:196-203 (2006)), due to its increased ability to disrupt and pass through the cell wall. The survival fraction and uptake (molecules/cell) of *C. albicans* was determined for PD1 mediated by the 3 different PSs with or without A16 pre-incubation for various time periods ranging between 1-24 hours. *C. albicans* was incubated with 100 μM RB, 100 μM ce6, or 10 μM PEI-ce6 for 30 min in either the presence or absence of a sub-inhibitory concentration (4 μg/mL) of A16 and received increasing fluences of 540 nm or 660 nm of light. The light-dependent killing of *C. albicans* in the presence of A16 was 2 to 5 logs greater than the killing at the same fluence in the absence of A16 for both RB and ce6 (FIG. 4, panels a, b). There was virtually no effect on the yeast cells either in the presence or absence of light. Killing by PEI-ce6 mediated PDI does not change dramatically after pre-incubation with the compound (FIG. 4, panel c). This observation is consistent with the fact that PEI-ce6, due to its polycationic charge, is self sufficient in bypassing the cell permeability barrier.

In order to confirm that the increase in phototoxicity observed by combining the different PS with A16 is actually due to an increase of cellular uptake of the PS by the cells and to document that the antifungal efficacy of saponins against *C. albicans* is associated with increased permeability, the amount of dye within the cell was measured by fluorescence spectrofluorimetry.

Cell suspensions ($10^8$ cells/mL) were incubated in the dark as above using the same concentrations as for the PDI assays measured as μM PS equivalent (final concentration in incubation medium). Incubations were carried out in triplicate. Cell suspensions were centrifuged (12000 rpm, 1 min) and washed twice in 1 mL sterile PBS. The cell pellet was dissolved in 1.5 mL 0.1 M NaOH/1% SDS for 24 h to yield a homogenous solution. Uptake was determined by measurement of fluorescence in black 96-well flat-bottom plates (Costar) in a final volume of 200 μL using a Spectramax Gemini spectrofluorimeter (Molecular Devices) at 400 nm$_{ex}$/580-700 nm$_{em}$ for ce6, PEI-ce6 and 552 nm$_{ex}$/555-620 nm$_{em}$ for RB. Uptake values were obtained as previously described (Tegos et al., Antimicrob Agents Chemother, 50:196-203 (2006)).

The cellular uptake of dye can be expressed as molecules per cell by correlation of the extracted PS concentration with the number of *C. albicans* cells present. In each case the addition of compound A16 dramatically increased the uptake of PS by the cells, and these differences were statistically significant (Table 3).

TABLE 3

Uptake assessment of photosensitizers in the presence of the natural product A16.

| | PS | +A16 (1 hr) | +A16 (24 hrs) |
|---|---|---|---|
| RB | 3.8 ± 0.6 | 4.55 ± 0.5* | 9.12 ± 0.22** |
| ce6 | 0.81 ± 0.06 | 3.1 ± 0.25** | 9.1 ± 0.15** |
| PEI-ce6 | 13.4 ± 1.1 | 20.9 ± 1.3** | 23.0 ± 0.7** |

Values represent the uptake in molecules/cell from pellets obtained after incubation of the cell suspensions with different PS with or without A16 at the same concentrations used for PDI studies. Values are the means of three determinations + standard deviation. The yeast cell density was, $10^8$ CFU/ml.
**P < 0.01; and,
*P < 0.1; compared with the uptake values of PS alone.

The influx of the PS ce6 into *C. albicans* cells was further examined and confirmed by confocal laser scanning microscopy. Alone, ce6 demonstrated no apparent internalization into either yeast or pseudohyphae *C. albicans* cells after one hour incubation (FIG. 5, panel a). However, when ce6 and A16 are incubated together for one hour, internalization of ce6 is visible (FIG. 5, panel b). Consistent with the PDI assays, after a 24 hour incubation period there was a dramatic increase in the concentration of ce6 inside the fungal cells in both yeast form (FIG. 5, panel c) and, in particular, pseudohyphae (FIG. 5, panel d), further confirming the ability of A16 to increase cell permeability.

The pore-forming characteristic of saponins makes them ideally suited for use with conventional antifungal therapy. Compound A16 was able to increase uptake of PS enabling much increased PDI of the fungus. Here we show that saponins in conjunction with PDT may be used for treatment of *C. albicans* infections. This study is the first to demonstrate that RB and ce6 in the presence with a saponin have a dramatic PDI effect to fungal cells (FIG. 4, panels a-c; FIG. 5, panels a-d; Table 3). Furthermore, the dramatic increase in permeability of pseudohyphae (FIG. 5, panel d), when compared to *C. albicans* cells in the yeast morphology (FIG. 5, panel c), suggests the previously observed decrease in biofilm formation in the presence of the saponin (FIG. 3) is due to an increase in permeability of pseudohyphae and hyphae.

Example 5

Interaction Between A16 and Fluconazole

Since compound A16 was able to facilitate uptake of PS compounds, we investigated their ability to increase uptake to the commonly used antifungal agent fluconazole. As indicated above, fluconazole and saponins have different target sites, although they both function by altering the fungal cell membrane. Interestingly, when we exposed fungi to different concentrations of fluconazole and A16, we found that a sub-inhibitory concentration of compound A16 (4 μg/mL) was able to decrease the MIC of *C. albicans* isolate DAY185 from 2 μg/mL for fluconazole alone to 1 μg/mL for a combination of the two compounds. Despite less growth in the well resulting in a "speckled" pattern, the two *C. albicans* isolates with increased resistance to fluconazole showed no increase in sensitivity to fluconazole treatment in the presence of A16. One of the molecular mechanisms responsible for increased resistance to fluconazole for isolate 98-145 is a homozygous V437I point mutation in the ERG11 gene (White et al., Antimicrob Agents Chemother, 46:1704-1713 (2002)). This suggests that the alteration of the fluconazole target site still renders the fungus resistant despite a potential increase in influx of fluconazole caused by addition of compound A16.

The saponins were able to inhibit growth of several *C. albicans* isolates, including isolates which were resistant to fluconazole and echinocandins (Table 2). Whether or not *C. albicans* can develop resistance to saponins is not known. Since saponins are synthesized mostly by plants, plant pathogenic fungi have developed resistance mechanisms to these natural products (Osbourn, Trends Plant Sci, 1:4-9 (1996)). There are several mechanisms in which phytopathogenic fungi evade saponin toxicity, ranging from avoidance to enzymatic degradation (Osbourn, Trends Plant Sci, 1:4-9 (1996)). Studies using *S. cerevisiae* and the saponin α-tomatine from tomato have shown that the fungus has greater inhibition to a degradation product, tomatidine, than to the complete α-tomatine saponin (Simons et al., Antimicrob Agents Chemother, 50:2732-2740 (2006)), suggesting that if *C. albicans* gains/evolves the ability to detoxify saponins, it may still be inhibited by the degradation products.

The abundance of saponin derived natural products and the lack of overt cellular toxicity displayed by the majority of compounds in this study suggests saponins may provide a promising source of new antifungal agents. These compounds represent an opportunity to expand the current classes of antifungal agents in use and to improve available antifungal drugs by exploiting these new chemical scaffolds. Future studies will focus on defining the minimal structural components required to retain full inhibitory and protective effects against *C. albicans*.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method of treating a fungal infection in a subject, the method comprising administering to the subject a therapeutically effective amount of a compound of Formula II:

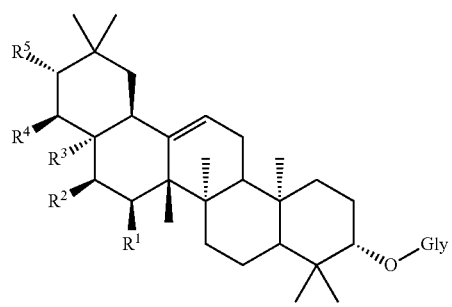

or a pharmaceutically acceptable salt thereof, wherein:
$R_1$ is H or $OC(O)R^A$;
$R_2$ is H or OH;
$R_3$ is H, $C(O)OR^A$, $CH_2OR^A$, $CH_2OC(O)R^A$;
$R_4$ and $R_5$ are each independently H or $OC(O)R^B$;
$R^A$ is H or $C_{1-6}$ alkyl;
$R^B$ is $C_{2-6}$ alkenyl; and
Gly is

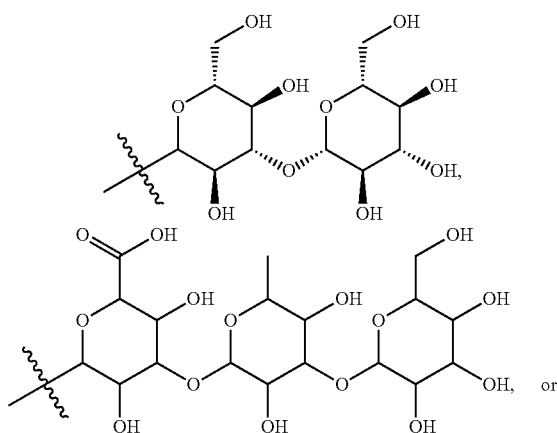

-continued
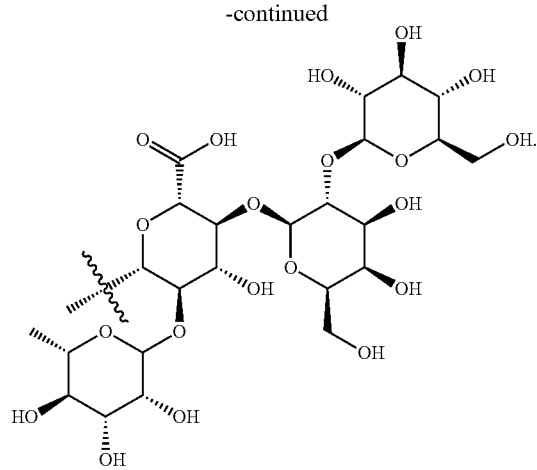
2. The method of claim 1, wherein the compound is:
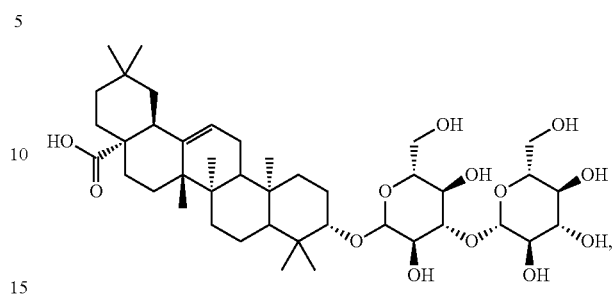
or a pharmaceutically acceptable salt thereof.
3. The method of claim 1, wherein the compound is:
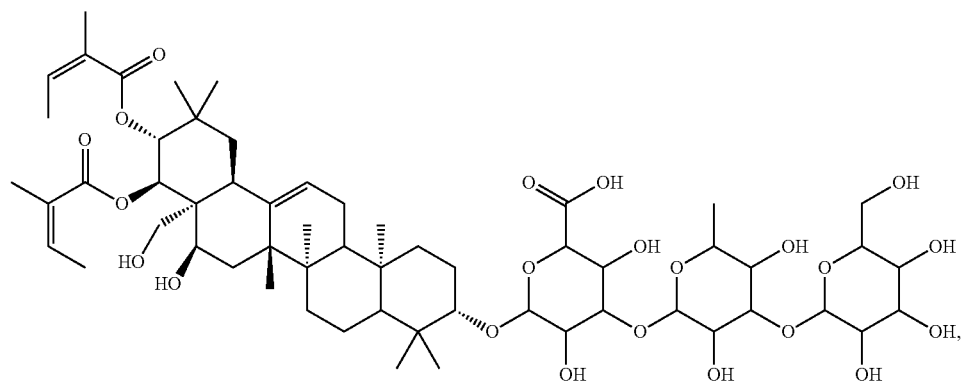
or a pharmaceutically acceptable salt thereof.
4. The method of claim 1, wherein the compound is:
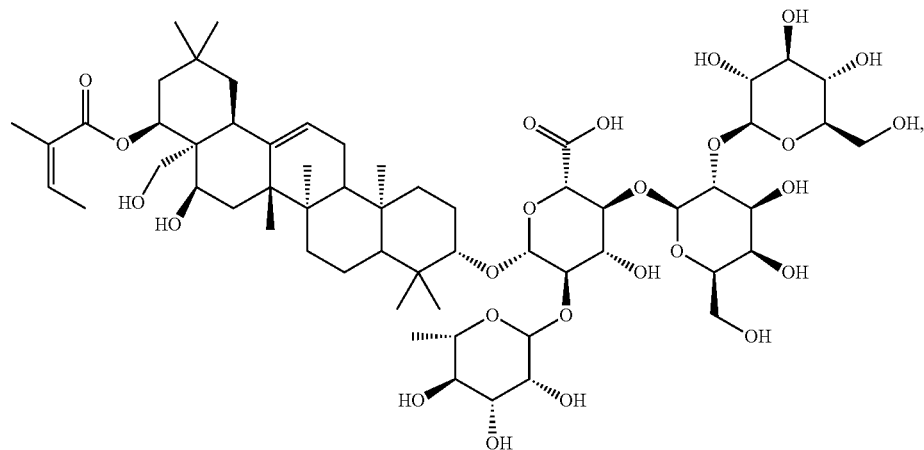
or a pharmaceutically acceptable salt thereof.

5. The method of claim 1, wherein the compound is:
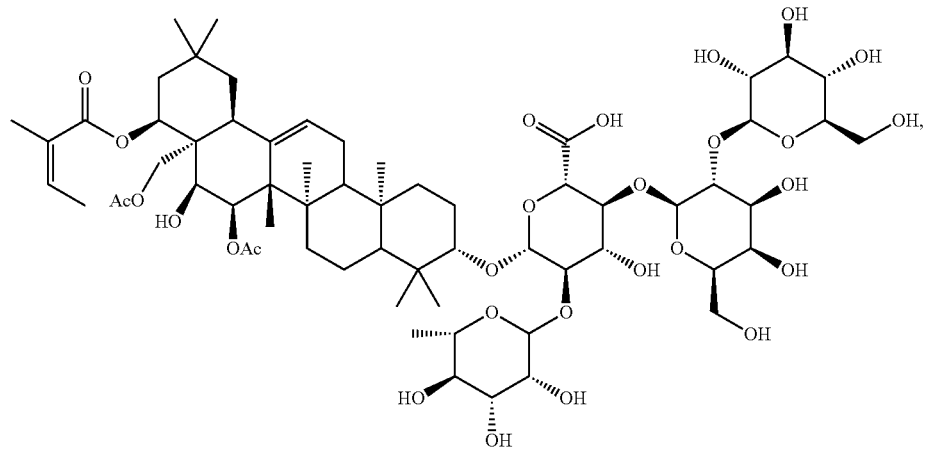
or a pharmaceutically acceptable salt thereof.
6. The method of claim 1, wherein the fungal infection is infection with a *Candida* species fungus.
* * * * *